(12) United States Patent
Kato et al.

(10) Patent No.: US 11,187,519 B2
(45) Date of Patent: Nov. 30, 2021

(54) IMAGING METHOD AND IMAGING APPARATUS

(71) Applicant: SCREEN HOLDINGS CO., LTD., Kyoto (JP)

(72) Inventors: Keisuke Kato, Kyoto (JP); Naoki Ishikawa, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 327 days.

(21) Appl. No.: 16/477,412

(22) PCT Filed: Dec. 27, 2017

(86) PCT No.: PCT/JP2017/046889
§ 371 (c)(1),
(2) Date: Jul. 11, 2019

(87) PCT Pub. No.: WO2018/150744
PCT Pub. Date: Aug. 23, 2018

(65) Prior Publication Data
US 2019/0376781 A1 Dec. 12, 2019

(30) Foreign Application Priority Data
Feb. 17, 2017 (JP) .............................. JP2017-027520

(51) Int. Cl.
*G01B 9/02* (2006.01)
*A61B 3/10* (2006.01)
*A61B 5/00* (2006.01)

(52) U.S. Cl.
CPC .......... *G01B 9/02063* (2013.01); *A61B 3/102* (2013.01); *A61B 5/0066* (2013.01); *G01B 9/02091* (2013.01)

(58) Field of Classification Search
None
See application file for complete search history.

(56) References Cited

U.S. PATENT DOCUMENTS 6,172,752 B1    1/2001   Haruna et al.
8,274,660 B2 *  9/2012   Sugita ................ G01B 9/02044
                                                     356/479

(Continued)

FOREIGN PATENT DOCUMENTS

JP    05-071912 A    3/1993
JP    10-325795 A    12/1998

(Continued)

OTHER PUBLICATIONS

International Search Report issued in corresponding International Patent Application No. PCT/JP2017/046889, dated Mar. 27, 2018, with English Translation.

(Continued)

*Primary Examiner* — Kaitlin A Retallick
(74) *Attorney, Agent, or Firm* — McDermott Will & Emery LLP

(57) ABSTRACT

In an OCT imaging, a focus position in a tomographic image is determined by a first distance, a second adjustment amount, a third adjustment amount and a refractive index of a medium. The first distance is a distance between a first surface and a second surface of a wall part of a container. The second adjustment amount is a focus position adjustment amount of an objective optical system at which an intensity of reflected light from the second surface is maximized when a reference mirror is positioned at a position where an object optical path length to the first surface and a reference optical path length are equal in a condition that the objective optical system is focused on the first surface. The third adjustment amount is a focus position adjustment amount in the imaging.

13 Claims, 12 Drawing Sheets

(56) References Cited

U.S. PATENT DOCUMENTS

| | | | |
|---|---|---|---|
| 9,585,555 B2 | 3/2017 | Dziubak et al. | |
| 2003/0199758 A1 | 10/2003 | Nelson | |
| 2005/0168751 A1* | 8/2005 | Horii | A61B 5/0062 |
| | | | 356/479 |
| 2005/0280830 A1 | 12/2005 | Rembe | |
| 2006/0256343 A1 | 11/2006 | Choma et al. | |
| 2010/0007894 A1 | 1/2010 | Suehira | |
| 2011/0222070 A1 | 9/2011 | Nagai et al. | |
| 2012/0320339 A1 | 12/2012 | Yonezawa | |
| 2013/0146768 A1* | 6/2013 | Sekiguchi | G01N 21/4795 |
| | | | 250/338.1 |
| 2015/0260503 A1* | 9/2015 | Osawa | G01B 9/02083 |
| | | | 356/479 |
| 2016/0007847 A1 | 1/2016 | Dziubak et al. | |
| 2016/0265899 A1* | 9/2016 | Minemura | G01B 9/02063 |
| 2018/0055365 A1 | 3/2018 | Ishikawa | |

FOREIGN PATENT DOCUMENTS

| | | |
|---|---|---|
| JP | 2000-056236 A | 2/2000 |
| JP | 2001-141652 A | 5/2001 |
| JP | 2001-212086 A | 8/2001 |
| JP | 3642996 B2 | 4/2005 |
| JP | 2005-523455 A | 8/2005 |
| JP | 2006-010693 A | 1/2006 |
| JP | 2010-019636 A | 1/2010 |
| JP | 2013-000223 A | 1/2013 |
| JP | 2015-178981 A | 10/2015 |
| JP | 2016-019635 A | 2/2016 |
| JP | 2018-036171 A | 3/2018 |
| JP | 6444080 B2 | 12/2018 |
| WO | 2006/078839 A3 | 7/2006 |
| WO | 2010/050296 A1 | 5/2010 |

OTHER PUBLICATIONS

D.V. Lyakin et al., "Longitudinal correlation properties of an optical field with broad angular and frequency spectra and their manifestation in interference microscopy", Optical Fields, Quantum Electronics, 2013, vol. 43, No. 10, pp. 949-957.

Extended European Search Report issued in corresponding European Patent Application No. 17896375.7-1020, dated Oct. 26, 2020.

Chinese Office Action issued in corresponding Chinese Patent Application No. 201780083485.7, dated Apr. 2, 2021, with Engish translation.

* cited by examiner

IMAGING METHOD AND IMAGING APPARATUS

CROSS REFERENCE

This application is the U.S. National Phase under 35 US.C. § 371 of International Application No. PCT/JP2017/046889, filed on Dec. 27, 2017, which claims the benefit of Japanese Application No. 2017-027520, filed on Feb. 17, 2017, the entire contents of each are hereby incorporated by reference.

TECHNICAL FIELD

This invention relates to a technique for imaging by detecting an interference light component of reflected light from an imaging object and reference light. Particularly, the invention relates to a technique for imaging an imaging object via an optically transparent wall part of a container.

BACKGROUND ART

In the technological fields of medicine and biochemistry, cells and microorganisms cultured in containers are observed. A technique for imaging cells or the like using a microscope or the like has been proposed as a method for observation without affecting cells or the like serving as an observation object. One of such techniques utilizes an optical coherence tomography (OCT) technique. This technique obtains and tomographically images an intensity distribution of reflected light from an imaging object in a depth direction by causing low coherence light emitted from a light source to be incident as illumination light on an imaging object and detecting interference light of reflected light (signal light) from the imaging object and reference light having a known optical path length.

In the OCT imaging technique, a set position of a focal point of an objective optical system for condensing signal light reflected from an imaging object and a set position of a reference plane (also called a coherence gate) are known as factors that affect image quality. The reference plane is a virtual plane on an optical path of the signal light where an optical path length of the signal light and an optical path length of the reference light are equal. Light including detailed information of the imaging object is signal light from the vicinity of a focus position, and light from which information of the imaging object can be accurately extracted by increasing an intensity of interference light is signal light from the vicinity of the reference plane. Thus, these set positions need to be adjusted to obtain good image quality. However, from a tomographic image obtained by imaging, it is difficult to read at which positions a focal point and a reference plane were located when this image was imaged. Therefore, it is not easy for a user not having a detailed knowledge to properly set these positions.

A technique for obtaining a tomographic image having desired quality by adjusting a difference between an optical path length of signal light and that of reference light is, for example, described in patent literature 1. This technique is such that the position of a coherence gate is imaged while being changed in multiple steps and an optimal position of the coherence gate is obtained from images obtained in each imaging. This technique assumes an imaging apparatus for ophthalmology and a disclosed apparatus images a retina.

CITATION LIST

Patent Literature

[PTL 1] JP 2016-019635A

SUMMARY OF INVENTION

Technical Problem

In imaging an imaging object such as cells carried in a container, imaging may be performed via an optically transparent wall part (e.g. a bottom part) of a container. In such a case, signal light is condensed via the container wall part. A focus position on the imaging object may be different from a focus position when the signal light is condensed without via the container due to the refraction of the signal light in the container. Further, containers having various thicknesses of wall parts and various refractive indices can be used. A method for grasping a focus position in a tomographic image in such a case has not been established yet. Thus, the problem has been that the adjustment of the focus position and the optical path length of the reference light is more difficult.

Solution to Problem

This invention was developed in view of the above problem and aims to provide a technique for imaging an imaging object in a container utilizing the interference of reflected light from the imaging object and reference light, the technique being capable of specifying a focus position in a tomographic image imaged via a wall part of the container.

One aspect of this invention is directed to an imaging method for tomographically imaging an imaging object in a medium carried in a container having an optically transparent wall part, the imaging method including a step of causing one branch light branched from low coherence light emitted from a light source to be incident on the imaging object, causing interference of signal light obtained by condensing reflected light from the imaging object via the wall part by an objective optical system and reference light obtained by reflecting another branch light by a reference mirror and obtaining an interference signal corresponding to a detection result of interference light, a step of obtaining a reflected light intensity distribution of the imaging object based on the interference signal and generating a tomographic image from the reflected light intensity distribution, and a step of specifying a focus position of the objective optical system in the tomographic image.

Further, another aspect of this invention is directed to an imaging apparatus for tomographically imaging an imaging object in a medium carried in a container having an optically transparent wall part, the imaging apparatus including a imaging unit which causes one branch light branched from low coherence light emitted from a light source to be incident on the imaging object, detects interference light generated by interference of signal light obtained by condensing reflected light from the imaging object via the wall part by an objective optical system and reference light obtained by reflecting another branch light by a reference mirror and outputs an interference signal corresponding to the detected interference light, a signal processor which obtains a reflected light intensity distribution of the imaging object based on the interference signal and generates a tomographic image from the reflected light intensity distribution, a focus position adjuster which changes a focus position of the objective optical system in an optical axis direction of the objective optical system, a mirror position adjuster which changes a position of the reference mirror in a direction along an optical path of the reference light, and a focus position calculator which calculates a focus position of the objective optical system in the tomographic image.

In these inventions, to achieve the above object, when an object optical path length is defined as an optical path length of the signal light, a reference optical path length is defined as an optical path length of the reference light, a first adjustment amount is defined as a focus position adjustment amount of the objective optical system when the objective optical system is focused on a first principal surface on a side of the objective optical system out of principal surfaces of the wall part, a second adjustment amount is defined as a focus position adjustment amount of the objective optical system at which an intensity of reflected light from a second principal surface on a side of the imaging object out of the principal surfaces of the wall part is maximized when the reference mirror is positioned at a position where the reference optical path length is equal to the object optical path length to the first principal surface with the focus position adjustment amount of the objective optical system set at the first adjustment amount, and a first distance is defined as a distance between the first principal surface and the second principal surface in an optical axis direction of the objective optical system in the reflected light intensity distribution obtained from the interference signal, a position where a distance to the first principal surface in the optical axis direction in the reflected light intensity distribution obtained from the interference signal obtained with the focus position adjustment amount of the objective optical system set at a third adjustment amount, the second adjustment amount being between the first adjustment amount and the third adjustment amount, is a second distance expressed by a sum of a value obtained by multiplying a difference between the third adjustment amount and the second adjustment amount by a square of a refractive index of the medium and the first distance is set as a focus position of the objective optical system in the tomographic image corresponding to the reflected light intensity distribution.

Here, the "focus position adjustment amount" means a movement amount of the focus position in the air obtained by operating the objective optical system. For example, if the focus position adjustment amount is changed from the first adjustment amount to the second adjustment amount, the focus position changes by an amount equivalent to a difference between the first adjustment amount and the second adjustment amount in the air. On the other hand, the focus position in the case of focusing in the medium in the container via the wall part of the container does not match the focus position and a change amount in the air due to refractive indices of the container and the medium.

If light passes through the wall part of the container, an optical path length of the light and a physical length can be converted from one into the other via the refractive index of the container. In the case of the invention, a change amount of the focus position adjustment amount and a change amount of the focus position can be converted from one into the other via the refractive index of the container. However, since the thickness and the refractive index of the container vary, it is difficult to accurately specify the focus position in the tomographic image.

In the invention, the focus position in the tomographic image can be specified as follows. First, the focus position adjustment amount of the objective optical system when the objective optical system is focused on the first principal surface on the side of the objective optical system out of the principal surfaces of the wall part is referred to as the first adjustment amount. Since the reflected light from the first principal surface does not pass through the inside of the container, the object optical path length at that time is not affected by the refractive index of the container. Thus, the position of the reference mirror for matching the object optical path length and the reference optical path length at this time is also easily obtained.

In the reflected light intensity distribution obtained from the interference light detected with the reference mirror positioned at such a position, a component corresponding to the reflected light from the first principal surface appears at a depth position of 0. Further, a component corresponding to the reflected light from the principal surface on the side opposite to the first principal surface out of the principal surfaces of the wall part, i.e. the second principal surface on the side of the imaging object, should appear at a position distant from the first principal surface by a distance corresponding to the thickness of the wall part. This distance represents an optical path length difference between the first principal surface and the second principal surface, i.e. an optical thickness of the wall part and is obtained by multiplying a physical thickness of the wall part by the refractive index. This value is the first distance of the invention.

Further, if the position of the reference mirror is fixed, a component corresponding to the reflected light from the second principal surface in the reflected light intensity distribution is maximized when the objective optical system is focused on the second principal surface. If the focus position adjustment amount at which such conditions are obtained is obtained, the focus position adjustment amount for focusing the objective optical system on the second principal surface can be specified. This is referred to as the second adjustment amount. A value obtained by multiplying a difference between the first adjustment amount and the second adjustment amount by the refractive index represents a physical distance between the focus positions when the objective optical system is focused on the first principal surface and the second principal surface respectively, i.e. the thickness of the wall part.

It is considered to specify from these pieces of information where an actual focus position was located in the tomographic image obtained with the focus position adjustment amount set at the third adjustment amount. Note that the position of the imaging object in the depth direction in the tomographic image varies depending on the setting of the reference optical path length during imaging. More generally, it is sufficient to specify a focus position as a relative position with respect to the position of a component corresponding to a reference object whose physical position is known in a reflected light intensity distribution serving as a basis of a tomographic image. This is because these relative positions are determined by an object optical path length difference between the both and does not depend on the setting of the reference optical path length.

Here, the first principal surface of the container is used as a reference. The position adjustment amount of the focus position for focusing the objective optical system on the first principal surface and the position of the reference mirror for matching the object optical path length and the reference optical path length are already known. Accordingly, if the focus position can be expressed on the basis of the first principal surface, an absolute focus position in the tomographic image can be specified from a relationship between the position of the reference mirror at this time and the position of the reference mirror during imaging.

First, a distance between the second principal surface and the focus position in the reflected light intensity distribution is considered. Since the wall part of the container is not present between the second principal surface and the focus position, it is sufficient to consider only the light passing through the medium carried in the container. A physical change amount of the focus position in the medium when the position adjustment amount is changed from the second adjustment amount for focusing on the second principal surface to the third adjustment amount is obtained by multiplying the difference between the second adjustment amount and the third adjustment amount by the refractive index of the medium.

On the other hand, in the reflected light intensity distribution, a distance between the position where the component corresponding to the second principal surface appears and the focus position is expressed by a product of the physical distance between the both and the refractive index of the medium. Since the physical distance between the both is obtained by multiplying the difference between the second adjustment amount and the third adjustment amount by the refractive index of the medium as described above, a value obtained by multiplying the difference between the second adjustment amount and the third adjustment amount by a square of the refractive index of the medium represents the distance between the second principal surface and the focus position in the reflected light intensity distribution. By adding the first distance, which is a distance between the first principal surface and the second principal surface in the reflected light intensity distribution, to this distance, the focus position on the basis of the first principal surface is obtained.

If the focus position in the reflected light intensity distribution is specified in this way, at which position focusing is achieved in the tomographic image can be, for example, clearly specified. In this way, a user can perform, for example, an operation of moving the focus position to a desired position in the imaging object while viewing the tomographic image. Further, where the focus position is displayed in the tomographic image depends on the reference optical path length during imaging. Thereby, a display position of the focus position in the tomographic image can be arbitrarily set by settings to change the reference optical path length.

Advantageous Effects of Invention

As described above, according to the invention, a focus position in a reflected light intensity distribution can be specified as a relative position with respect to the position of the first principal surface. Since the focus position is specified based on information obtained from actually detected light, this method holds true even if the thickness and the refractive index of the container wall part are unknown.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DESCRIPTION OF EMBODIMENTS

Figure 1:
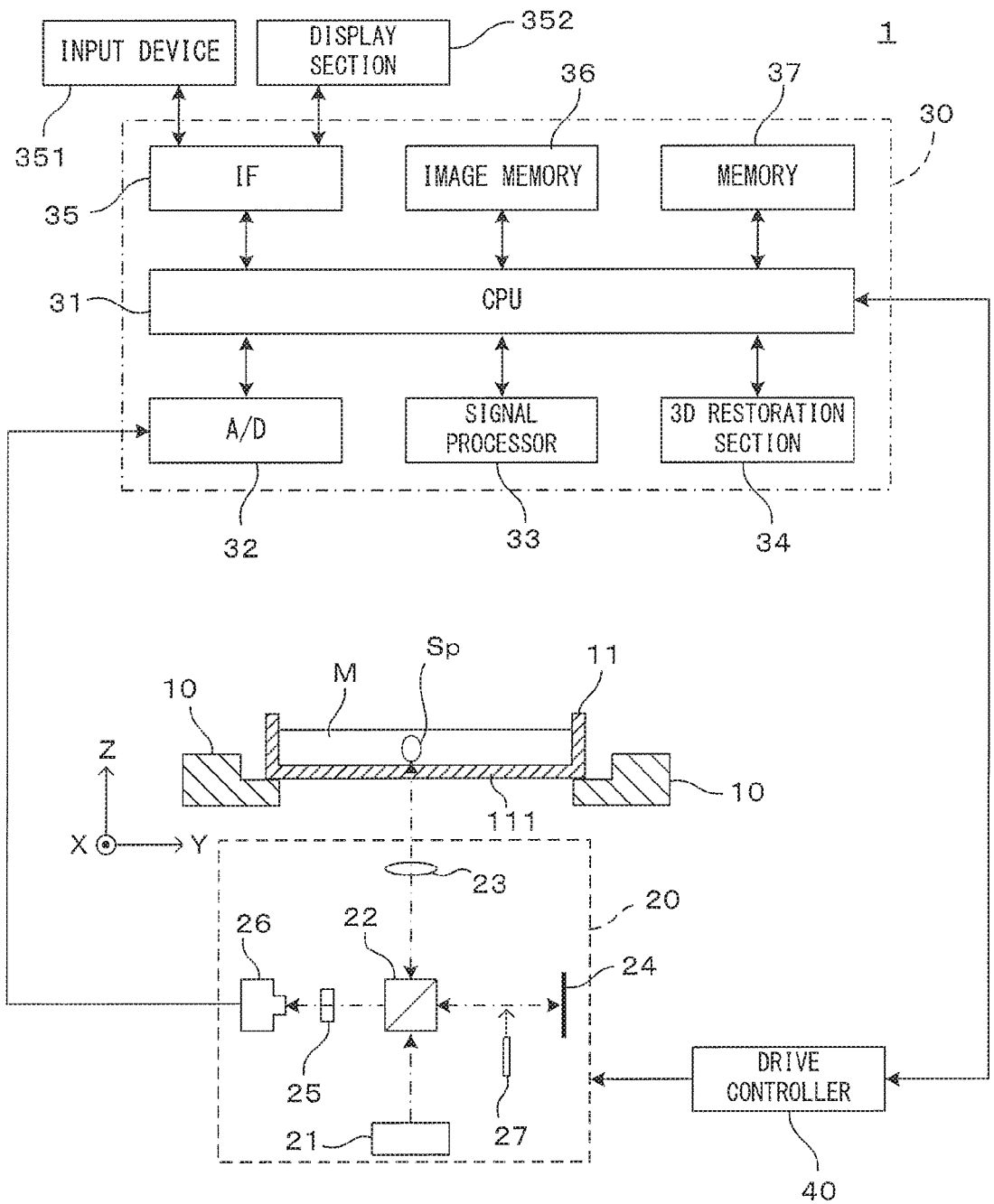
FIG. 1 is a drawing showing an embodiment of an imaging apparatus according to the present invention.

FIG. 1 is a drawing showing an embodiment of an imaging apparatus according to the present invention. The imaging apparatus 1 tomographically images a cell cultured in a culture medium M, a spheroid (cell aggregate) which consists of many cells, an organ-like structure (hereinafter, referred to as a "cell or the like" generically) as an imaging object, processes the obtained tomographic image and generates a stereoscopic image of the imaging object. Note that although an example of imaging a spheroid in the culture medium as the imaging object is illustrated here, the imaging object is not limited to this. For unified presentation of the directions in drawings, the XYZ orthogonal coordinate axes are established as shown in FIG. 1. The XY plane is a horizontal surface. The Z axis represents the vertical axis, in more detail, the (−Z) direction represents the vertically downward direction.

The imaging apparatus 1 comprises a holder 10. The holder 10 holds in an approximately horizontal posture a shall plate-like container 11 having a flat bottom surface made of transparent and uniform glass or resin and called a "dish" in such a manner that its opening is directed toward above. The container 11 has a flat bottom surface made of transparent and uniform glass or resin and is called a "dish". A predetermined amount of an appropriate culture medium M is poured in the container 11 in advance, and a spheroid Sp is cultured in the medium at the bottom part 111 of the container 11. Although FIG. 1 shows only one spheroid Sp, a plurality of spheroids Sp may be cultured in one container 11.

An imaging unit 20 is disposed below the container 11 which is held by the holder 10. An optical coherence tomography (OCT) apparatus capable of imaging tomographic images of an imaging object in a non-contact and non-destructive (non-invasive) manner is used as the imaging unit 20. As described in detail later, the imaging unit 20 which is an OCT apparatus comprises a light source 21 which emits illumination light for an imaging object, a beam splitter 22, an objective optical system 23, a reference mirror 24, a spectroscope 25, a photo-detector 26 and a shutter 27.

Further, the imaging apparatus 1 comprises a control unit 30 which controls operations of the apparatus and a drive controller 40 which controls movement of movable parts of the imaging unit 20. The control unit 30 comprises a CPU (Central Processing Unit) 31, an A/D convertor 32, a signal processor 33, a 3D restoration section 34, an interface (IF) section 35, an image memory 36 and a memory 37.

The CPU 31 governs operations of the entire apparatus by executing a predetermined control program. The control program executed by the CPU 31 and data which are generated during processing are saved in the memory 37. The A/D convertor 32 converts a signal which the photo-detector 26 of the imaging unit 20 outputs in accordance with the amount of received light into digital image data. The signal processor 33 performs image processing described later based upon a digital data outputted from the A/D converter 32, thereby generates a tomographic image of the imaging object. Based upon image data of a plurality of tomographic images, the 3D restoration section 34 generates a stereoscopic image (3D image) of the imaged cell aggregate. The image memory 36 saves the image data of the tomographic images generated by the signal processor 33 and the image data of the stereoscopic image generated by the 3D restoration section 34. The signal processor 33 and the 3D restoration section 34 may be configured as dedicated hardware. Further, these may be realized as software by a program executed by the CPU 31.

Further, the CPU 31 sends a control command to the drive controller 40, and the drive controller 40 makes the movable parts of the imaging unit 20 execute predetermined operation in accordance with the control command. As described next, the tomographic images of the spheroid (cell aggregate) which is the imaging object are obtained owing to combination of scan moving of the imaging unit 20 executed by the drive controller 40 and detection of the amount of the received light by the photo-detector 26.

Figure 2A:
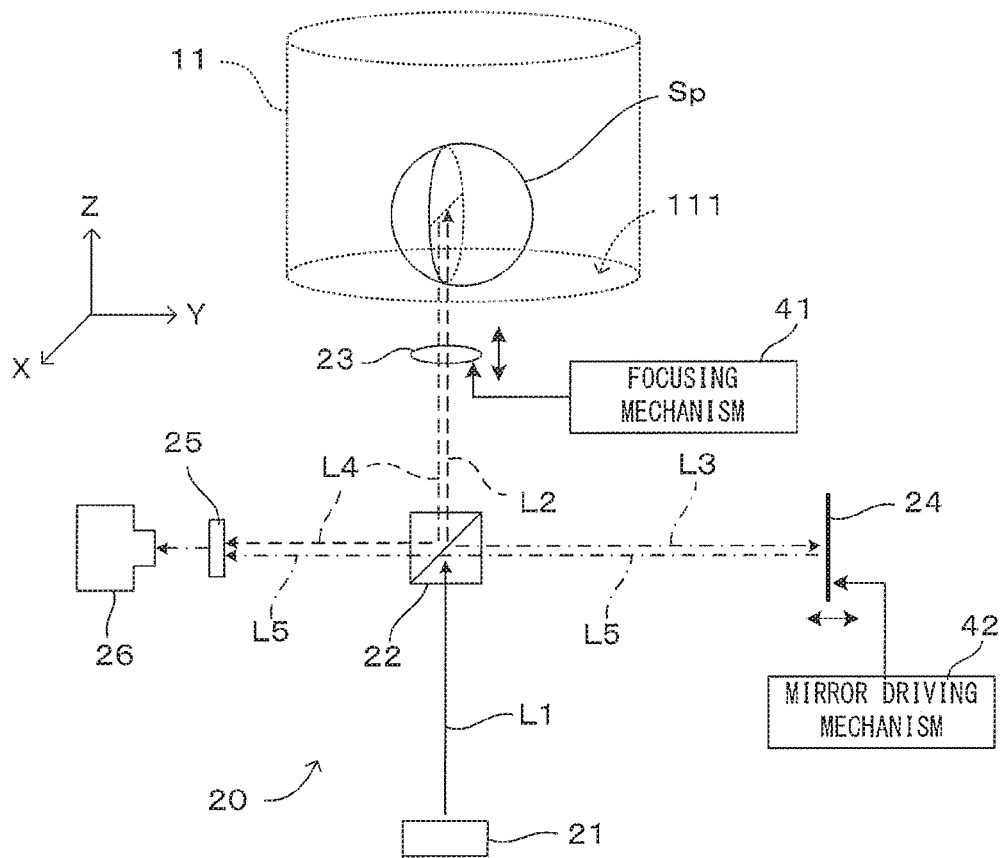
FIG. 2A is a drawing for describing the principle of imaging in this imaging apparatus.
Figure 2B:
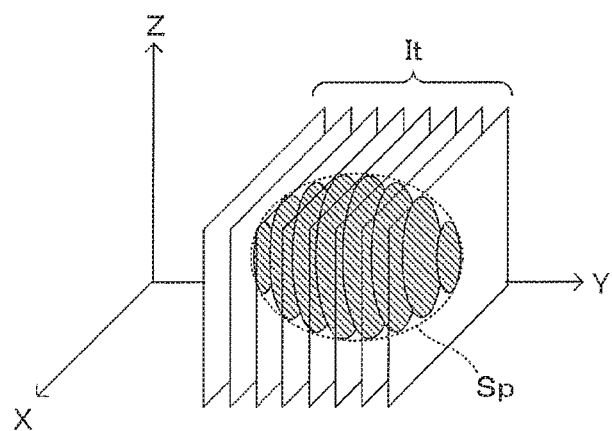
FIG. 2B is a drawing for describing the principle of imaging in this imaging apparatus.

FIGS. 2A and 2B are drawings for describing the principle of imaging in this imaging apparatus. More specifically, FIG. 2A is a drawing which shows optical paths inside the imaging unit 20, and FIG. 2B is a schematic drawing which shows tomographic imaging of a spheroid. As described earlier, the imaging unit 20 works as an optical coherence tomography (OCT) apparatus.

In the imaging unit 20, from the light source 21 which includes a light emitting element such as a light emitting diode or a super luminescent diode (SLD) for instance, a low-coherence light beam L1 containing a wide-range wavelength components is emitted. The light beam L1 impinges upon the beam splitter 22. Some light L2 indicated by the broken-line arrow propagates toward the well W, and some light L3 indicated by the arrow of long dashed short dashed line propagates toward the reference mirror 24.

The light L2 propagating toward the container 11 is incident on the container 11 by way of the objective optical system 23. More specifically, the light L2 emitted from the beam splitter 22 is incident on the bottom part 111 of the container 11 via the objective optical system 23. The objective optical system 23 has a function of converging the light L2 propagating from the beam splitter 22 toward the container 11 to the imaging object in the container 11 (spheroid Sp in this case) and a function of collecting the reflected light emitted from the imaging object and causing it to propagate toward the beam splitter 22. Although the objective optical system 23 is illustrated as a single objective lens in FIG. 2A, the objective optical system 23 may include a plurality of optical elements.

The objective optical system 23 is supported movably in the Z direction by a focusing mechanism 41 which is disposed to the drive controller 40. This enables the focus position of the objective optical system 23 with respect to the imaging object to be changed in the Z direction. Hereinafter, a focal position of the objective optical system in the depth direction (Z-direction) is referred to as a "focal depth". An optical axis of the objective optical system 23 is parallel to a vertical direction and, therefore, perpendicular to the bottom part 111 of the container 11 in the form of a flat plate. Further, an incident direction of illumination light on the objective optical system 23 is parallel to the optical axis. The arrangement of the objective optical system 23 is determined such that a light center of the light coincides with the optical axis.

If a user gives setting information about the focal depth via an input device 351, the focusing mechanism 41 changes the focus position of the objective optical system 23 in accordance with the setting information. Specifically, the user inputs a focus position adjustment amount, that is, a movement amount of the focus position of the objective optical system 23 from a predetermined initial position. The focusing mechanism 41 can change the focus position, for example, by moving an objective lens which is included in the objective optical system 23 in the optical axis direction. A configuration in which the focus position changes step-wise in a predetermined step may be used.

The incident light L2 via the bottom part 111 is reflected at the surface of the spheroid Sp unless the spheroid Sp transmits the light beam L2. On the other hand, when the spheroid Sp has a property of transmitting the light beam L2 to a certain extent, the light beam L2 propagates into inside the spheroid Sp and is reflected by a structure element which is inside the spheroid. When the near infrared rays for instance are used as the light beam L2, it is possible to allow the incident light to reach even inside the spheroid Sp. The reflected light from the spheroid Sp is irradiated as scattered light in various directions. Out of that, light L4 irradiated within a light collection range of the objective optical system 23 is collected by the objective optical system 23 and sent to the beam splitter 22.

The reference mirror 24 is supported movably by a mirror driving mechanism 42 provided in the drive controller 40 so that the reference mirror 24 is movable in a direction (Y direction in FIG. 2A) along the incident direction while a reflection surface thereof is perpendicular to an incident direction of the light L3. The light L3 incident on the reference mirror 24 is reflected by the reflection surface and propagates toward the beam splitter 22 as light L5 propagating in an opposite direction along an incident optical path. This light L5 becomes reference light. By changing the position of the reference mirror 24 by the mirror driving mechanism 42, an optical path length of the reference light changes. The position of the reference mirror 24 is changed not only automatically in accordance with a purpose of the imaging, but arbitrarily by the setting input from the user via the input device 351.

An openable and closable shutter 37 is disposed on the optical path of the reference light L3. L5. The shutter is controlled by the drive controller 40. In a state where the shutter 37 is closed by a control command from the drive controller 40, the shutter 37 shields the reference light L3 on the optical path of the reference light L3. Therefore, the incidence of the reflected light L5 by the reference mirror 24 to the beam splitter 22 does not occur. On the other hand, in a state where the shutter 27 is open, the reference light L3 is reflected by the reference mirror 24 and thereby enters the beam splitter 22 as the reflected light L5.

The reflected light L4 reflected by a surface or an internal reflecting surface of the spheroid Sp and reference light L5 reflected by the reference mirror 24 are incident on the photo-detector 26 via the beam splitter 22. At this time, interference due to a phase difference between the reflected light L4 and the reference light L5 occurs, but an optical spectrum of interference light differs depending on a depth of the reflecting surface. That is, the optical spectrum of the interference light has information on a depth direction of the imaging object. Thus, a reflected light intensity distribution in the depth direction of the imaging object can be obtained by spectrally diffracting the interference light at each wavelength to detect a light quantity and Fourier transforming a detected interference signal. An OCT imaging technique based on such a principle is called Fourier domain OCT (FD-OCT).

The imaging unit 20 of this embodiment is provided with a spectroscope 25 on an optical path of the interference light from the beam splitter 22 to the photo-detector 26. A spectroscope utilizing a prism, a spectroscope utilizing a diffraction grating and the like can be, for example, used as the spectroscope 25. The interference light is spectrally diffracted for each wavelength component and received by the photo-detector 26.

By Fourier-transforming the interference signal output from the photo-detector 26 according to the interference light detected by the photo-detector 26, the reflected light intensity distribution of the spheroid Sp in the depth direction, i.e. in the Z direction at the incident position of the light beam L2 is obtained. By scanning the light beam L2 incident on the container 11 in the X direction, the reflected light intensity distribution in a plane parallel to an XZ plane is obtained, with the result that a tomographic image of the spheroid Sp having this plane as a cross-section can be generated. In this specification, a series of operations for obtaining one tomographic image It in a cross-section parallel to the XZ plane by beam scanning in the X direction is referred to as one imaging.

Images are obtained by changing the incident position of the light L2 along the Y direction over multiple steps and imaging a tomographic image for every change. As shown in FIG. 2B, a number of tomographic images It of the spheroid Sp are obtained along cross-sectional surfaces which are parallel to the XZ plane. As the scan pitch in the Y direction is reduced, it is possible to obtain image data with sufficient resolution to grasp the stereoscopic structure of the spheroid Sp. Scan movements of the light beam in X and Y direction are realized as an optical device (not shown) changing an optical path such as a Galvanometer mirror changes the incident position of the light beam to X and Y direction, the container 11 carrying the spheroid Sp and imaging unit 20 relatively move to X and Y direction or the like.

Note that, in the imaging unit 20 of the above description, it is the beam splitter 22 that has a function of dividing the light from the light source 21 to the illumination light and the reference light and a function of mixing the signal light and the reference light to cause interference. On the other hand, some of OCT imaging apparatuses are known to have a dividing/mixing function, for example, an optical fiber coupler as described below.

Figure 3A:
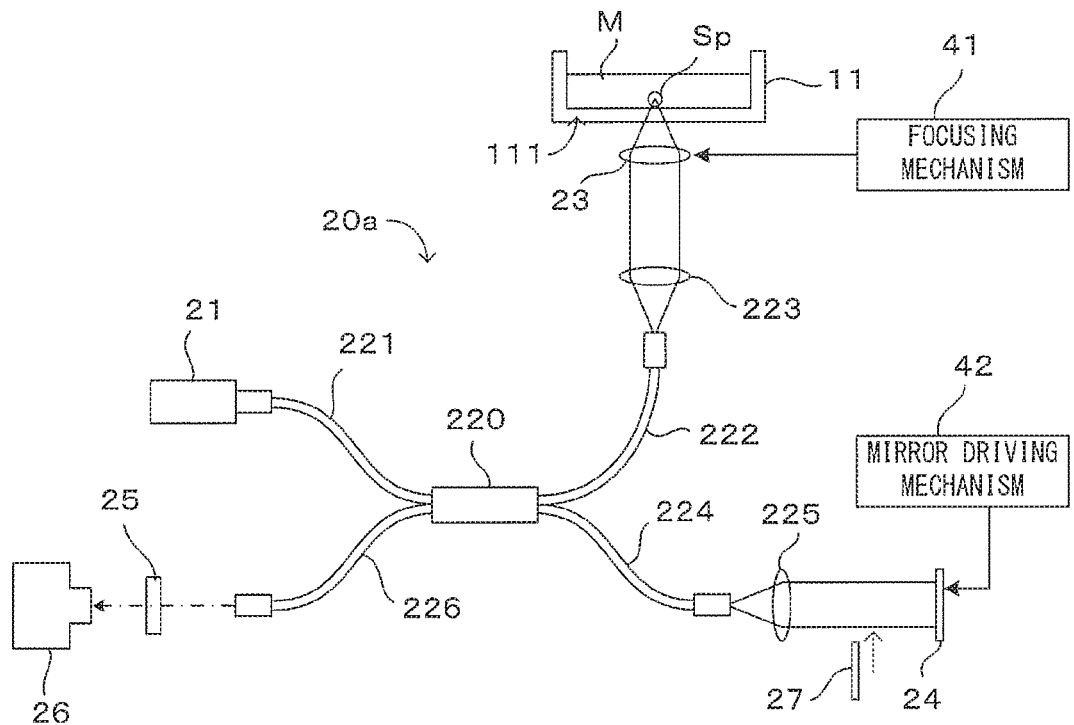
FIG. 3A is a diagram showing other configuration examples of the OCT apparatus.
Figure 3B:
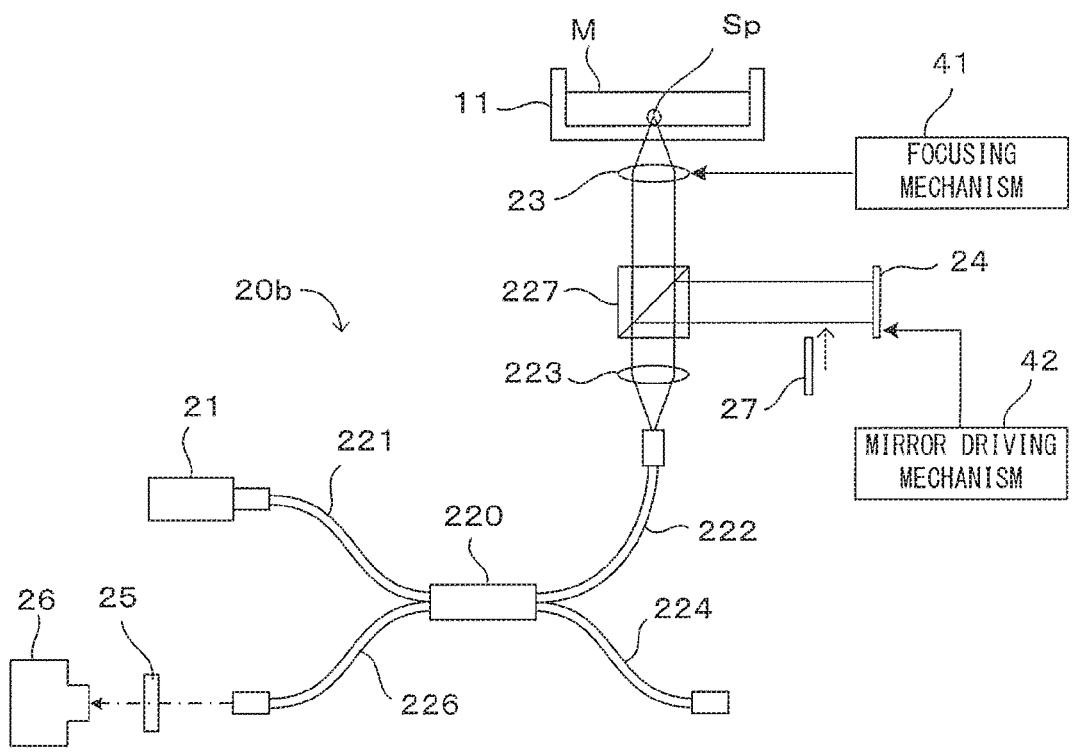
FIG. 3B is a diagram showing other configuration examples of the OCT apparatus.

FIGS. 3A and 3B are diagrams showing other configuration examples of the OCT apparatus. Note that, in the following description, constituent components same as or corresponding to those of other embodiments are denoted by the same reference signs to facilitate understanding. The structures and functions thereof are basically the same as those of the embodiment unless particularly described, and thereby the detail description is omitted. An OCT imaging principle for detecting interference light by the optical fiber coupler is not described in detail since it is same as the above embodiment.

In an example shown in FIG. 3A, an imaging unit 20a includes an optical fiber coupler 220 instead of the beam splitter 22 as a dividing/mixing optical device. One 221 of optical fibers constituting the optical fiber coupler 220 is connected to a light source 21 and low-coherence light emitted from the light source 21 is branched into lights to two optical fibers 222, 224 by the optical fiber coupler 220. The optical fiber 222 constitutes an object side optical path. More specifically, light emitted from an end part of the optical fiber 222 is incident on an objective optical system 23 via a collimator lens 223. Reflected light (signal light) from an imaging object is incident on the optical fiber 222 via the objective optical system 23 and the collimator lens 223.

Another optical fiber 224 constitutes a reference side optical path. More specifically, light emitted from an end part of the optical fiber 224 is incident on a reference mirror 24 via a collimator lens 225. Reflected light (reference light) from the reference mirror 24 is incident on the optical fiber 224 via the collimator lens 225. The signal light propagating in the optical fiber 222 and the reference light propagating in the optical fiber 224 interfere in the optical fiber coupler 220. The interference light is incident on a photo-detector 26 via an optical fiber 226 and a spectroscope 25. An intensity distribution of the reflected light on the imaging object is obtained from the interference light received from the photo-detector 26 as in the above principle.

Also in an example shown in FIG. 3B, an optical fiber coupler 220 is provided in an imaging unit 20b. However, an optical fiber 224 is not used and a collimator lens 223 and a beam splitter 227 as an optical device are provided on an optical path of light emitted from an optical fiber 222. As the principle described above, an objective optical system 23 and a reference mirror 24 are arranged on two optical paths branched by the beam splitter 227. In such a configuration, signal light and reference light are mixed by the beam splitter 227 and interference light generated thereby is guided to a photo-detector 26 through the optical fibers 222, 226.

In these examples, the optical path of each light propagating in a space is partially replaced by an optical fiber in the principle diagram of FIG. 1, but the operation principle is the same. Also in these examples, the focusing mechanism 41 moves the objective optical system 23 in directions toward and away from the container 11, whereby a focal depth of an objective optical system 23 with respect to the imaging object can be adjusted. Further, the mirror driving mechanism 42 moves the reference mirror 24 along the incident direction of the light, whereby the optical path length of the reference light can be changed.

An imaging operation by this imaging apparatus 1 is described below. The same imaging operation can be performed regardless of whether the imaging unit is configured to use the beam splitter or the optical fiber coupler described above.

Figure 4:
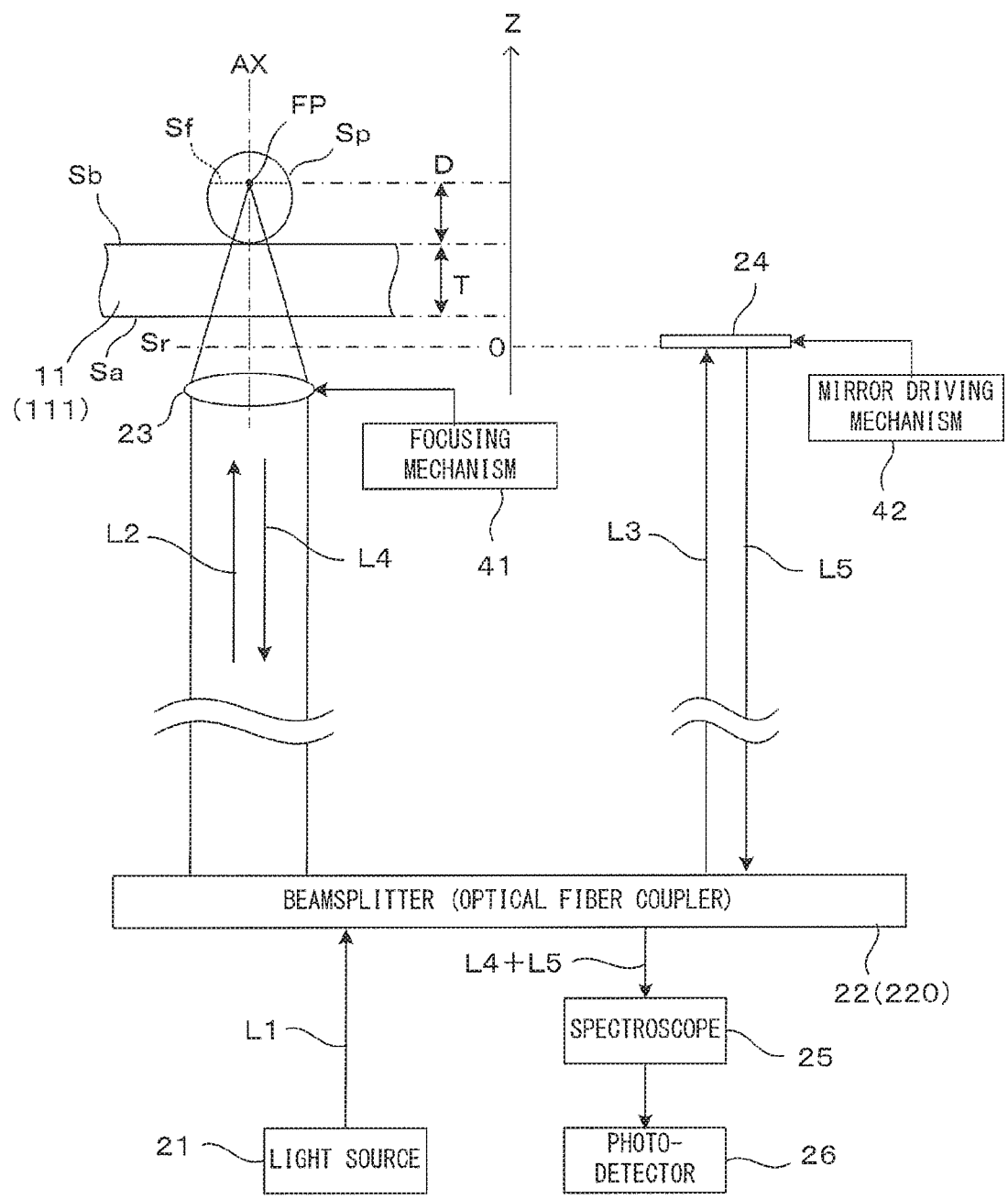
FIG. 4 is a diagram schematically showing a positional relationship between the focal depth of the objective optical system and a reference plane.
Figure 5:
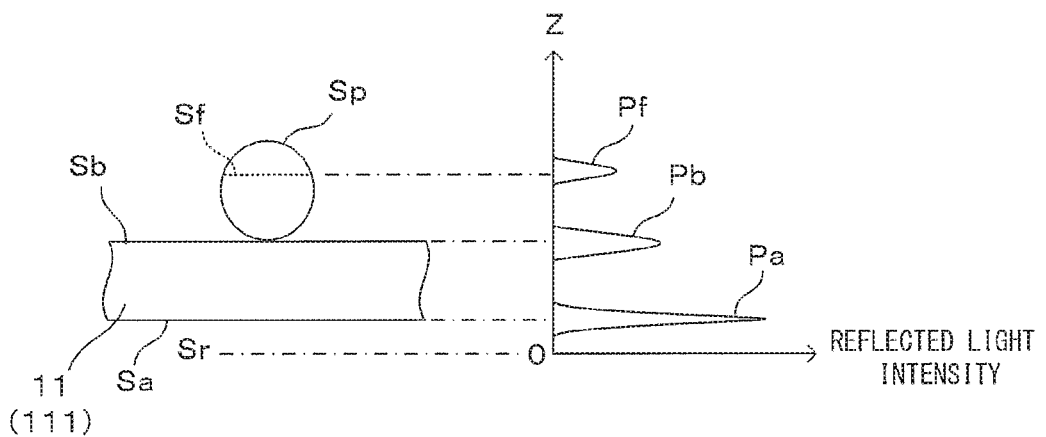
FIG. 5 is a diagram and a graph showing a relationship between the position of the reference plane and a reflected light intensity distribution.

FIG. 4 is a diagram schematically showing a positional relationship between the focal depth of the objective optical system and a reference plane. Further, FIG. 5 is a diagram and a graph showing a relationship between the position of the reference plane and a reflected light intensity distribution. In the OCT imaging apparatus, a position where an optical path length of signal light and that of reference light are equal is, in principle, a reference position in a depth direction of an image.

In the following description, in an objective optical path in which the illumination light L2 and the signal light L4 propagate via the objective optical system 23 as shown in FIG. 4, a reference plane Sr is defined as follows. Specifically, the reference plane Sr is a virtual plane corresponding to a reflecting surface of the reference mirror 24 in a reference optical path, i.e. located at a position where the optical lengths are equal. Further, a surface of the bottom part 111 of the container 11 on a side near the objective optical system 23 is referred to as a lower bottom surface Sa, and a surface on a side opposite to this, i.e. an inner bottom surface on a side near the spheroid Sp serving as the imaging object and in contact with the culture medium is referred to as an upper bottom surface Sb. Furthermore, a focal plane of the objective optical system 23, i.e. a plane including an object-side focal point FP of the objective optical system 23 and perpendicular to an optical axis AX of the objective optical system 23, is denoted by reference sign Sf. Further, in the following description, an optical path length in the objective optical path is referred to as an "object optical path length" and an optical path length in the reference optical path is referred to as a "reference optical path length".

Further, for an explanation described later, reference sign T denotes a distance between the lower bottom surface Sa and the upper bottom surface Sb, i.e. a thickness of the container bottom part 111. Further, reference sign D denotes a distance between the upper bottom surface Sb and the focal plane Sf, i.e. a distance from the inner bottom surface of the container 11 to the focal point FP. This distance D can also be defined as a focal depth of the objective optical system 23 when the inner bottom surface (upper bottom surface Sb) of the container 11 is a starting point.

If a virtual reflecting surface is located on the reference plane Sr in the objective optical path, an optical path length (object optical path length) of light reflected by this reflecting surface is equal to an optical path length (reference optical path length) of light reflected by the reflecting surface of the reference mirror 24. The position in the depth direction of each reflecting surface near the imaging object is expressed by a distance from the reference plane Sr in the Z direction.

If the imaging object (spheroid Sp) has a reflecting surface on the focal plane Sf, a signal having an intensity corresponding to a reflected light intensity from the reflecting surface appears at a depth position corresponding to a distance from the reference plane Sr to this reflecting surface (i.e. focal plane Sf) in the reflected light intensity distribution after the Fourier transform. In the actual imaging object, signals corresponding to reflected light from reflecting surfaces at various depths appear at respective positions and those signals are superimposed in the reflected light intensity distribution. However, only the signal from the reflecting surface on the focal plane Sf is considered here to facilitate understanding.

The flat surfaces Sa, Sb of the container bottom part 111 are also strong reflecting surfaces and signals corresponding to these appear respectively at positions corresponding to distances from the reference plane Sr in the reflected light intensity distribution. For example, as shown in FIG. 5, in the reflected light intensity distribution, a signal Pf corresponding to the focal plane Sf, a signal Pa corresponding to the lower bottom surface Sa and a signal Pb corresponding to the upper bottom surface Sb appear respectively at positions corresponding to distances from the reference plane Sr.

The "distance" in this case is, strictly speaking, an optical path length difference. Thus, a physical distance of each surface on the objective optical path passing through the container and the culture medium M having refractive indices different from a refractive index of air is not necessarily equal to an optical distance of each surface shown in the reflected light intensity distribution. The refractive index of air is substantially 1. On the other hand, refractive indices of glass, acrylic resin and the like widely used as materials of the container 11 are larger than the refractive index of air and are about 1.5, and a refractive index of water as a main component of the general culture medium M is about 1.33.

The refractive index of air is approximated to 1, that of the container 11 is denoted by reference sign Nc and that of the culture medium M is denoted by reference sign Ns. Further, if the imaging object is cells or the like, a refractive index thereof is known to be hardly different from that of water. Accordingly, it is assumed below that a refractive index of the spheroid Sp serving as the imaging object is also equal to that of the culture medium M.

Figure 6:
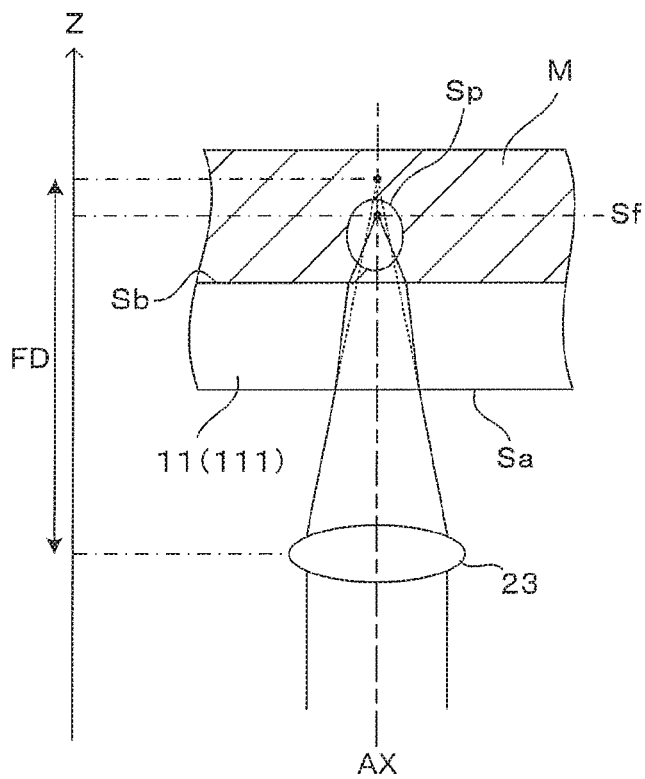
FIG. 6 is a diagram schematically showing an optical path in the case of condensing light via the container.

FIG. 6 is a diagram schematically showing an optical path in the case of condensing light via the container. As described above, the refractive index Nc of the container 11 is higher than that of air and the refractive index Ns of the culture medium M and the spheroid Sp is lower than the refractive index Nc of the container 11. Thus, as shown in FIG. 6, light is refracted respectively by an interface between the lower bottom surface Sa of the container 11 and the air and an interface between the upper bottom surface Sb and the culture medium M. Therefore, a depth of the focal plane Sf of the objective optical system 23 when viewed from the objective optical system 23 is a depth different from the focal length FD in the air.

As just described, the focus position varies due to refraction by the surfaces of the container 11 and a variation mode thereof changes according to the material and thickness of the container bottom part 111. Thus, the user cannot accurately know at which position focusing is achieved in a tomographic image obtained by imaging. Further, an adjustment amount of the focus position of the objective optical system 23 and a change amount of the focus position in the imaging object do not match. Thus, the user cannot understand which input should be set and given to the objective optical system 23 to achieve focusing at a desired position.

If it becomes clear at which position a tomographic image is focused to be imaged, it is convenient for the user to adjust the focus position and the reference optical path length. To this end, the focus position in the tomographic image needs to be specified, also taking into account the influence of refraction in imaging via the container 11. The principle and specific processing contents of a focus position specifying process of this embodiment enabling this are described below.

Figure 7:
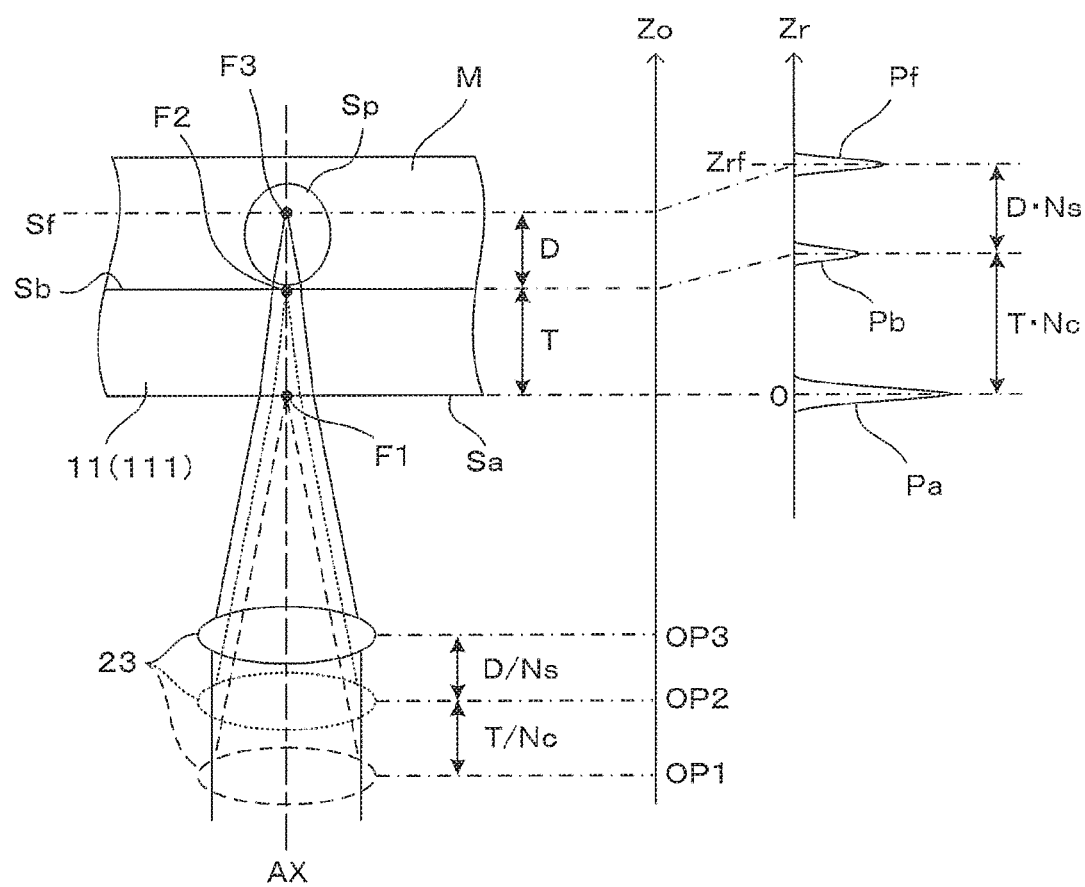
FIG. 7 is a diagram showing the principle of the focus position specifying process.

FIG. 7 is a diagram showing the principle of the focus position specifying process. As shown in FIG. 7, a case where the objective optical system 23 is focused on a point F1 on the lower bottom surface Sa of the container 11, a case where the objective optical system 23 is focused on a point F2 on the upper bottom surface Sb of the container 11 and a case where the objective optical system 23 is focused on an arbitrary point F3 in the culture medium M are hypothetically assumed. A horizontal plane including the point F3 is equivalent to the focal plane Sf when the objective optical system 23 is focused in the culture medium. Further, OP1, OP2 and OP3 respectively denote focus position adjustment amounts of the objective optical system 23 for focusing on the points F1, F2 and F3.

As shown in FIG. 4, a physical thickness of the container bottom part 111 is denoted by reference sign T and a physical distance between the upper bottom surface Sb of the container 11 and the focal plane Sf is denoted by reference sign D. Further, the refractive index of the container 11 is denoted by reference sign Nc and that of the culture medium M (and the spheroid Sp) is denoted by reference sign Ns.

Not that, as described above, a physical length of an optical path and an optical path length do not necessarily match in light propagating via substances having different refractive indices. Thus, a coordinate axis representing a physical distance in the Z direction and a coordinate axis representing an optical distance corresponding to the optical path length are respectively distinguished by Zo and Zr below if necessary.

A case is considered where the focus position is changed from a state where the objective optical system 23 is focused on the lower bottom surface Sa of the container 11, and the objective optical system 23 is focused on the upper bottom surface Sb. A movement amount of the focus position at this time is equal to the thickness T of the container bottom part 111. On the other hand, the focus position adjustment amount of the objective optical system 23 to realize this movement is expressed by the following equation:

$$|OP2-OP1|=T/Nc \qquad (1)$$

using the refractive index Nc of the substance filling up this interval.

Similarly, a case is considered where a state where the objective optical system 23 is focused on the point F2 of the upper bottom surface Sb of the container 11 is changed to a state where the objective optical system 23 is focused on the point F3. A movement amount of the focus position at this time is equal to the distance D between the upper bottom surface Sb of the container 11 and the focal plane Sf. On the other hand, the focus position adjustment amount of the objective optical system 23 to realize this movement is expressed by the following equation:

$$|OP3-OP2|=D/Ns \qquad (2)$$

using the refractive index Ns of the substance filling up this interval.

Next, positions are considered where signal components corresponding to the respective surfaces Sa, Sb and Sf appear in a profile of a reflected light intensity distribution obtained from detected interference light. Intervals between the respective signal components are equivalent to optical path lengths between the respective surfaces. Thus, a distance between the signal Pa corresponding to the lower bottom surface Sa and the signal Pb corresponding to the upper bottom surface Sb is a value T·Nc obtained by multiplying the physical distance T between the both by the refractive index Nc between the both. Similarly, a distance between the signal Pb corresponding to the upper bottom surface Sb and the signal Pf corresponding to the focal plane Sf is a value D·Ns obtained by multiplying the physical distance D between the both by the refractive index N between the both.

Absolute positions where the respective signal components appear in the coordinate axis Zr representing the reflected light intensity distribution change according to the position of the reference plane, but the distances between the respective signal components do not change. Accordingly, it is sufficient if the focus position in the profile of the reflected light intensity distribution can be expressed as a relative position corresponding to a specific signal component appearing in the profile. The focus position can be expressed, for example, on the basis of the lower bottom surface Sa of the container 11. If this position is assumed as an origin, a focus position Zrf can be expressed by the following equation:

$$Zrf=D \cdot Ns + T \cdot Nc \qquad (3)$$

as is clear from FIG. 7. By substituting the equation (2) into this equation, the following equation is obtained:

$$Zrf=|OP3-OP2| \cdot Ns^2 + T \cdot Nc \qquad (4)$$

The first term on the right side of the equation (4) means that the distance from the upper bottom surface Sb of the container 11 to the focal plane Sf is expressed by the focus position adjustment amount during imaging with focusing achieved on the upper bottom surface Sb of the container 11 and the refractive index Ns of the culture medium M. Further, the second term on the right side expresses an optical thickness of the container bottom part 111.

The refractive index Ns is determined by the type of the culture medium M and a value thereof is known if the culture medium M is specified. Accordingly, if the focus position adjustment amount OP2 for focusing on the upper bottom surface Sb and the optical thickness T·Nc of the container bottom part 111 are known, the focus position Zrf in the tomographic image imaged with the arbitrary focus position adjustment amount OP3 can be obtained by the equation (4). Flows of specific processing contents for specifying these values are successively described below.

Figure 8A:
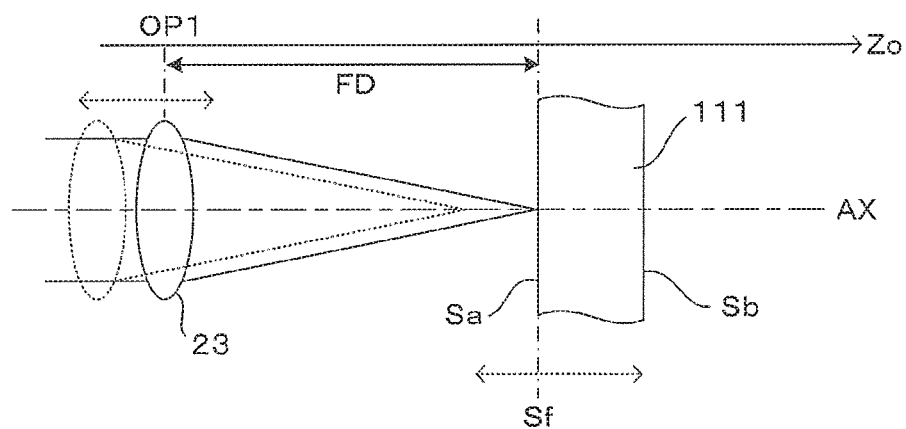
FIG. 8A is a diagram showing a process for specifying a condition of focusing the objective optical system on the lower bottom surface of the container.
Figure 8B:
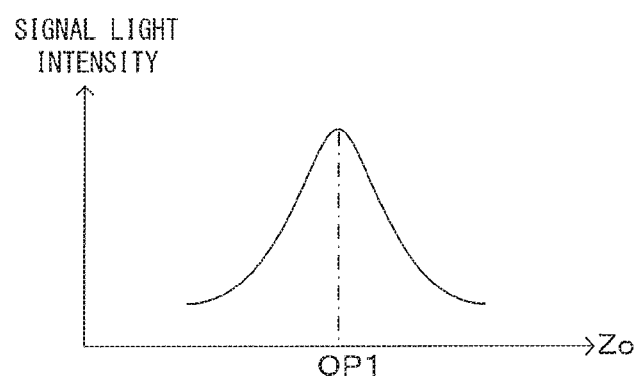
FIG. 8B is a graph showing a process for specifying a condition of focusing the objective optical system on the lower bottom surface of the container.

FIGS. 8A and 8B are a diagram and a graph showing a process for specifying a condition of focusing the objective optical system on the lower bottom surface of the container. First, the condition for focusing the objective optical system 23 on the lower bottom surface Sa of the container 11, specifically, the focus position adjustment amount OP1 for this focusing, is obtained. As shown in FIG. 8A, when a distance between the objective optical system 23 and the lower bottom surface Sa is equal to the focal length FD, the objective optical system 23 is focused on the lower bottom surface Sa. Such a focus position adjustment amount OP1 is obtained.

An intensity of signal light is detected while the focus position adjustment amount of the objective optical system 23 is changed near the lower bottom surface Sa as shown by dotted-line arrows in FIG. 8A. For example, the focus position can be scanned by bringing the objective optical system 23 closer to the lower bottom surface Sa from a state where the focus position is located in front of the lower bottom surface Sa. Since it is sufficient to consider only the propagation of light in the air in this state, a position adjustment can be relatively easily made if the focal length FD of the objective optical system 23 is known.

The signal light is detected with the shutter 27 for shielding the optical path of the reflected light closed. Accordingly, light incident on the photo-detector 26 is not the interference light of the signal light and the reference light, but only the signal light. The intensity of the signal light can be evaluated by an intensity of a specified wavelength component or a total, an integrated value or the like of intensities of the respective components, out of light incident on the photo-detector 26 from the spectroscope 25. As shown in FIG. 8B, the intensity of the signal light is maximized when the objective optical system 23 is focused on the lower bottom surface Sa. That is, a state where the intensity of the signal light is maximized can be regarded as an in-focus state. The focus position adjustment amount OP1 at this time is specified. This value OP1 is referred to as a "first adjustment amount" below.

Figure 9A:
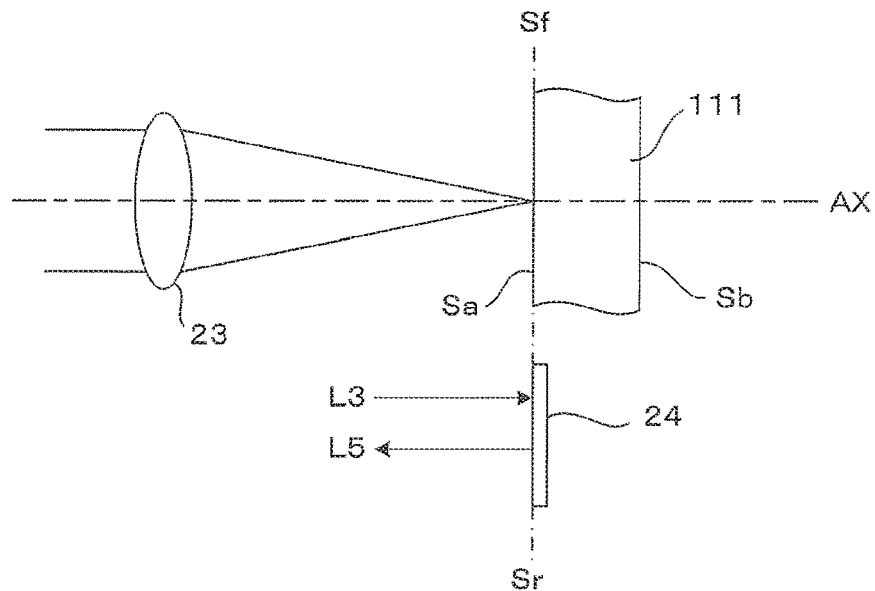
FIG. 9A is a diagram showing a process for specifying a condition of focusing the objective optical system on the upper bottom surface of the container.
Figure 9B:
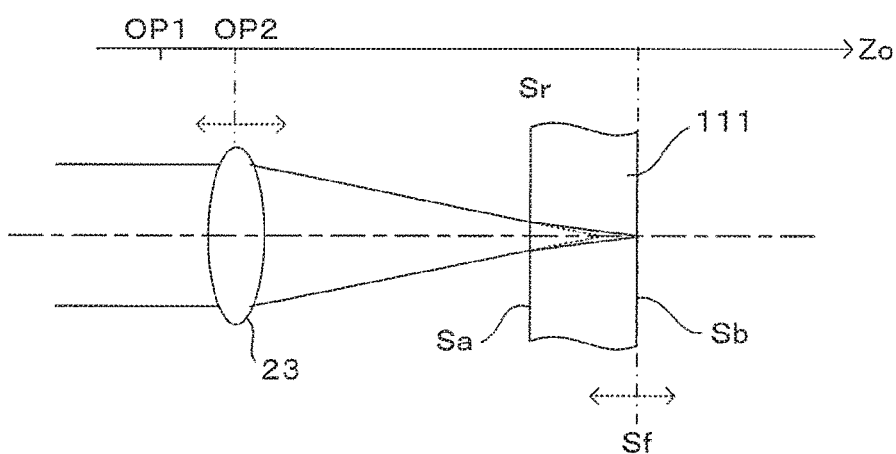
FIG. 9B is a diagram showing a process for specifying a condition of focusing the objective optical system on the upper bottom surface of the container.
Figure 9C:
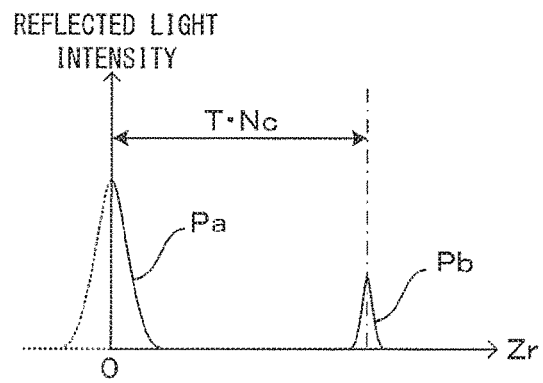
FIG. 9C is a graph showing a process for specifying a condition of focusing the objective optical system on the upper bottom surface of the container.

FIGS. 9A, 9B and 9C are diagrams and a graph showing a process for specifying a condition of focusing the objective optical system on the upper bottom surface of the container. As shown in FIG. 9A, the position of the reference mirror 24 is adjusted such that the object optical path length in the state where the objective optical system 23 is focused on the lower bottom surface Sa, which is found out as described above, and the reference optical path length match. Since the container 11 is not included in the objective optical path at this time, the respective optical path lengths can be easily matched by appropriately setting a focus position adjustment amount by the focusing mechanism 41 and a mirror position adjustment amount by the mirror driving mechanism 42. In this way, the reference plane Sr is set on the lower bottom surface Sa.

Detection by the photo-detector 26 is performed in this state. At this time, the shutter 27 is open and the interference light of the signal light and the reference light is incident on the photo-detector 26. The reflected light intensity distribution is obtained from the received interference light. Thus, the signal Pa from the lower bottom surface Sa located at the position of the reference plane Sr in the objective optical path appears at a depth position of 0 as shown in FIG. 9C. Further, the signal Pb from the upper bottom surface Sb appears at a position subsequent to this position. The distance between the signals Pa and Pb in the coordinate axis Zr obtained from such a profile is equivalent to the optical distance between the both, i.e. the optical thickness of the container bottom part 111. The value obtained in this way is the value T·Nc of the second term on the right side of the equation (4).

Further, the intensity of the signal Pb is maximized in the state where the objective optical system 23 is focused on the upper bottom surface Sb. Accordingly, the focus position adjustment amount of the objective optical system 23 when the intensity of the signal Pb is maximized can be specified by detecting the interference light and calculating the reflected light intensity distribution while changing the focus position adjustment amount of the objective optical system 23. The focus position adjustment amount at this time is the value OP2. This value OP2 is referred to as a "second adjustment amount" below.

If the respective values of OP1, OP2 and T·Nc are obtained, the thickness T of the container bottom part 111 and the refractive index Nc can be respectively uniquely obtained from those values and the equation (1). However, for the purpose of specifying the focus position shown by the equation (4), it is sufficient to obtain the optical thickness T·Nc of the container bottom part 111 and it is not always necessary to individually specify the thickness T and the refractive index Nc.

The focus position adjustment amount OP3 during imaging is a value appropriately set by the user. This value OP3 is referred to as a "third adjustment amount" below. The values OP2, T·Nc and Ns are already known by the processes thus far. Accordingly, the focus position Zrf in the reflected light intensity distribution can be specified for the arbitrarily set focus position adjustment amount OP3 by the equation (4). Not that, during imaging, the position of the reference plane Sr specifying the reference optical path length can be set independently of the focus position. A general formula which holds true for the set values of the arbitrary focus position adjustment amount (third adjustment amount) OP3 and the reference optical path length can be obtained as follows.

Figure 10A:
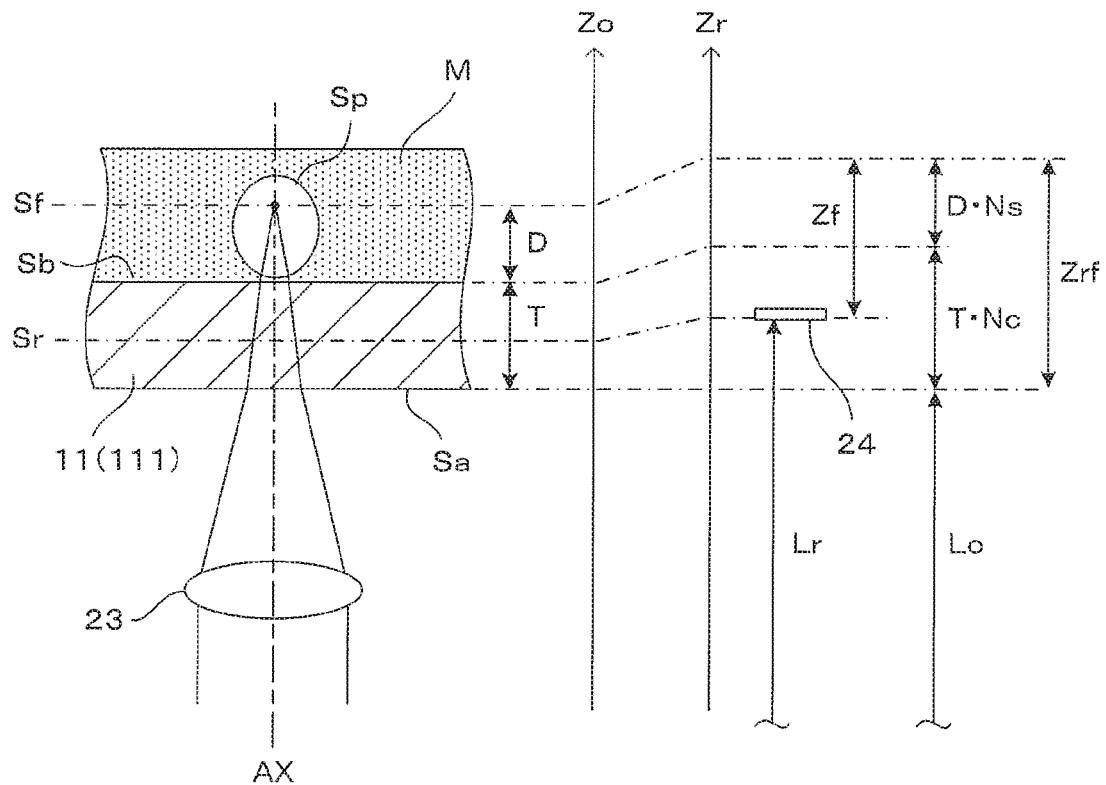
FIG. 10A is a diagram showing a relationship between the reference optical path length and the focus position.
Figure 10B:
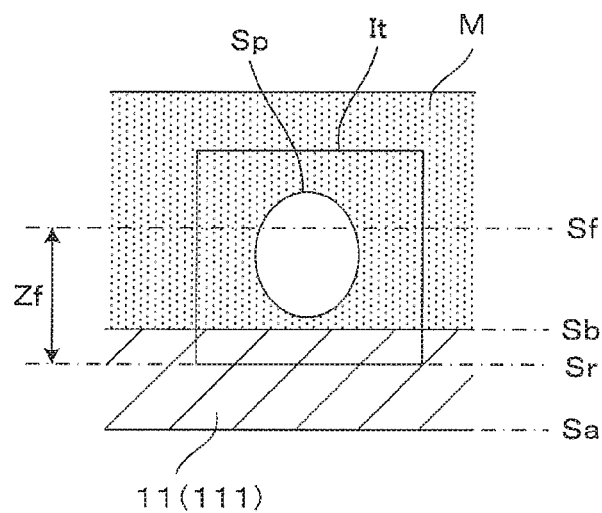
FIG. 10B is a diagram showing a relationship between the reference optical path length and the focus position.

FIGS. 10A and 10B are diagrams showing a relationship between the reference optical path length and the focus position. A basic concept is the same as above, but the position of the reference plane Sr, i.e. a reference optical path length Lr, can be arbitrarily set. A distance Zf to the focus position on the basis of the reference plane Sr in the reflected light intensity distribution is obtained. If Lo denotes an object optical path length to the lower bottom surface Sa of the container 11 in the objective optical path, the following equation is satisfied as is clear from the relationship shown in FIG. 10A.

$$Lr+Zf=Lo+Zrf=Lo+D\cdot Ns+T\cdot Nc=Lo+|OP3-OP2|\cdot Ns^2+T\cdot Nc \qquad (5)$$

The significance of this equation (5) is as follows.

As shown in FIG. 10B, a tomographic image It obtained from the reflected light intensity distribution includes an image of the imaging object in a predetermined imaging range with the reference plane Sr serving as one end of the image. In this tomographic image It, a distance from the image end corresponding to the reference plane Sr to the focus position, i.e. a focal depth in the image, is expressed by a value Zf in the equation (5). In this way, the focal depth Zf of the objective optical system 23 in the tomographic image It and the focus position adjustment amount OP3 and the reference optical path length Lr during imaging are associated by the equation (5).

Thus, it is, for example, possible to specify the in-focus position in the tomographic image from conditions during imaging. Accordingly, information representing the focus position can be, for example, added to the displayed tomographic image. In the FD-OCT imaging apparatus, a time delay from optical scanning of the imaging object to tomographic imaging can be reduced and the tomographic image can be displayed substantially in real time. If a line, a marker or the like indicating the in-focus position is displayed in the tomographic image displayed in real time, the user can adjust the focus position while viewing the image as in the case of microscope observation.

Further, even if the reference optical path length is changed for the purpose of changing the imaging range, for example, the relationship between the image end corresponding to the reference plane Sr and the focus position is obtained. Thus, a focus position can be accurately pointed out also in a tomographic image displayed after the change. Specifically, even if a range included in the tomographic image changes due to a change of the reference optical path length, the display position of the focus position can be changed, following this change.

Conversely speaking, the focus position can be moved with a distance between an image end and a displayed focus position kept constant. Specifically, by changing the reference optical path length Lr in accordance with the equation (5) such that the focus position Zf in the image is constant when the focus position adjustment amount OP3 of the objective optical system 23 is changed, the focus position in the tomographic image can be always constant. In this way, a request, for example, to constantly make a specific position (e.g. a center) in an image a focus position can be met.

Specifically, at which position of the imaged tomographic image the focus position is set can be determined, for example, by user settings. That is, if the user sets a distance from the image end to the focus position, the focus position in the image can remain unchanged even if the focus position is moved. In this case, if the user changes the focus position, the in-focus position for the imaging object moves, but the focus position in the tomographic image does not change. Thus, the image of the imaging object is scrolled in the depth direction according to a change of the focus position.

Further, in OCT imaging, image quality is best near the reference plane. By clarifying the relationship between the focus position and the position of the reference plane and controlling the distance between the both, the deterioration of image quality due to a deviation between these can be suppressed. Particularly, in the case of using an objective optical system having a large numerical aperture to enhance a resolution, an image possibly becomes unclear even near a reference plane by deviating from a depth of field range. By clearly specifying the focus position and the position of the reference plane by the equation (5), such a problem can be avoided. For example, in an imaging apparatus in which a focus position and a reference plane are changed according to a user operation, such an operation is possible in which an upper limit to a distance between the focus position and a reference plane is determined and settings beyond this are prohibited.

As just described, even if the thickness, the refractive index and the like of the container bottom part 111 are not known, information for specifying a focus position in a tomographic image can be obtained by conducting various measurements by causing illumination light to be incident on the container 11 used for imaging. Specific contents of a process for this are described below.

Figure 11:
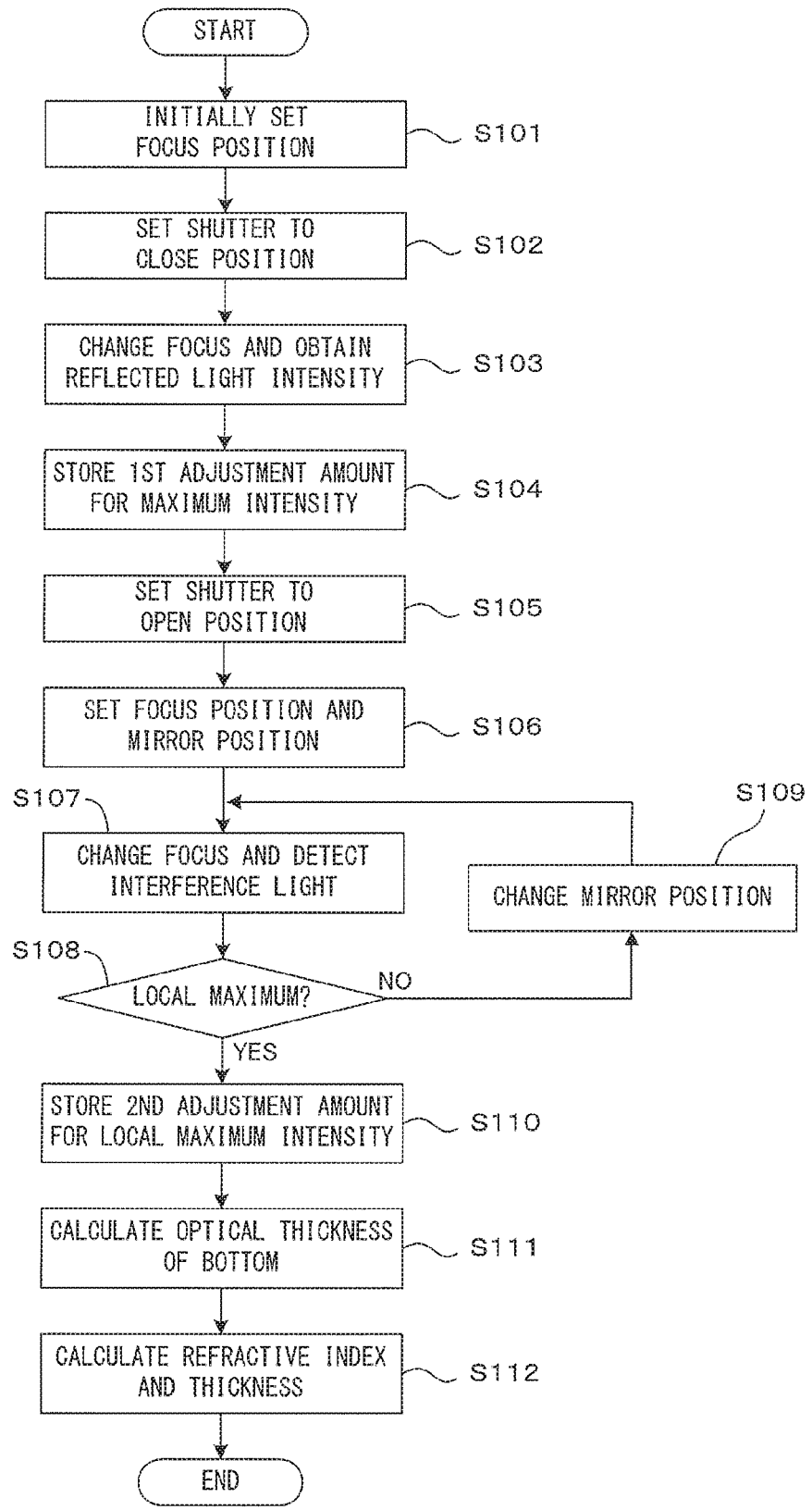
FIG. 11 is a flow chart showing the process for specifying the relationship between the focus position and the reference optical path length.

FIG. 11 is a flow chart showing the process for specifying the relationship between the focus position and the reference optical path length. As described later, this process is performed as a preprocessing of imaging for the imaging object after the container 11 carrying the culture medium M including the imaging object is set in the imaging apparatus 1. First, the focus position of the objective optical system 23 is initialized (Step S101). The focus position in an initial state may be automatically set to an appropriate position or may be set by an outlined adjustment operation by the user. In the case of automatic setting, such setting is desirable that the objective optical system 23 is focused at a position even below the lower bottom surface Sa of the container 11.

Further, the shutter 27 is positioned at a shielding position for shielding reference light on the reference optical path (Step S102).

From this state, the photo-detector 26 performs detection every time the focusing mechanism 41 changes and sets the focus position in multiple steps by driving the objective optical system 23 (Step S103). Since light in the reference optical path is shielded at this time, only reflected light from the reflecting surface on the objective optical path, i.e. only signal light is detected by the photo-detector 26. The lower bottom surface Sa of the container 11 generates most strong reflected light in the objective optical path, and a reflected light intensity is maximized when the objective optical system 23 is focused on the lower bottom surface Sa. Accordingly, it is assumed that the objective optical system 23 is focused on the lower bottom surface Sa when the intensity of the detected light is maximized, and the focus position adjustment amount at that time is stored as the first adjustment amount OP1 (Step S104).

Subsequently, the shutter 27 is positioned at a passage position which is deviated from the reference optical path and at which the reference light is passed (Step S105). Then, the focus position adjustment amount of the objective optical system 23 is set to the first adjustment amount OP1 and the position of the reference mirror 24 is set such that the object optical path length and the reference optical path length at this time are equal (Step S106). The reference optical path length at this time is equivalent to the value Lo in the equation (5). Since the objective optical path to the lower bottom surface Sa does not include the inside of the container, a condition for matching the object optical path length and the reference optical path length can be obtained in advance from mechanical dimensions of each part of the imaging unit 20. Further, this condition can also be obtained from a mechanical positional relationship between the focus position adjustment amount and the reference mirror position when the position of the lower bottom surface Sa and the position of the reference plane match in the reflected light intensity distribution.

Then, detection by the photo-detector 26 is performed while the focus position of the objective optical system 23 is changed upward, i.e. from the lower bottom surface Sa toward the upper bottom surface Sb of the container 11 in multiple steps. What is detected at this time is interference light obtained by synthesizing the signal light and the reference light. The signal processor 33 calculates a reflected light intensity distribution in the depth direction from a spectrum of the detected interference light (Step S107).

The upper bottom surface Sb of the container 11 is the reflecting surface closest to the lower bottom surface Sa. When the objective optical system 23 is focused on the upper bottom surface Sb, a most strong signal component appears at a position corresponding to the upper bottom surface Sb in the reflected light intensity distribution. Accordingly, an intensity of the signal component corresponding to the upper bottom surface Sb reaches a local maximum with focusing achieved on the upper bottom surface Sb when the reflected light intensity distribution is obtained by successively changing the focus position. If such a local maximum value is detected (YES in Step S108), it is assumed that focusing is achieved on the upper bottom surface Sb and the focus position adjustment amount at that time is stored as the second adjustment amount OP2 (Step S110). Further, a distance between the signal component Pa corresponding to the lower bottom surface Sa and the signal component Pb corresponding to the upper bottom surface Sb in the reflected light intensity distribution is stored as the optical thickness (T·Nc) of the container bottom part 111 (Step S111).

However, the local maximum value may not be possibly detected if the container bottom part 111 is thick. This is because the reference plane Sr is set on the lower bottom surface Sa of the container 11 in this stage and reflected light corresponding to the upper bottom surface Sb cannot be detected if the upper bottom surface Sb is located beyond a range where the interference of the signal light and the reference light can be caused. In such a case (NO in Step S108), the position of the reference mirror 24 is changed and photo-detection is performed again (Step S109).

Figure 12A:
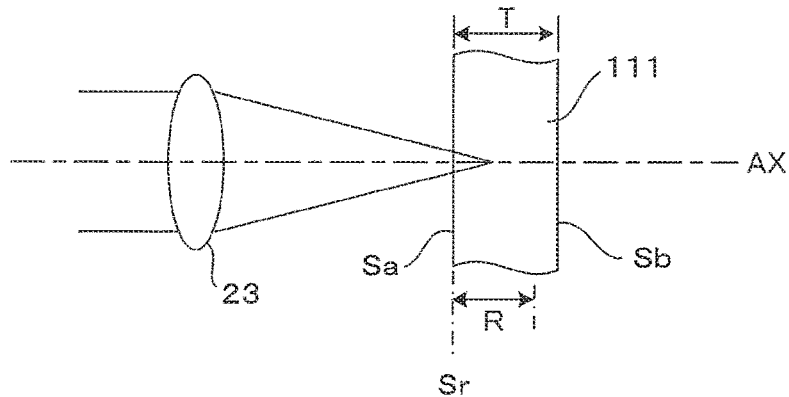
FIG. 12A is a diagram showing how to obtain the optical thickness when the container bottom part is thick.
Figure 12B:
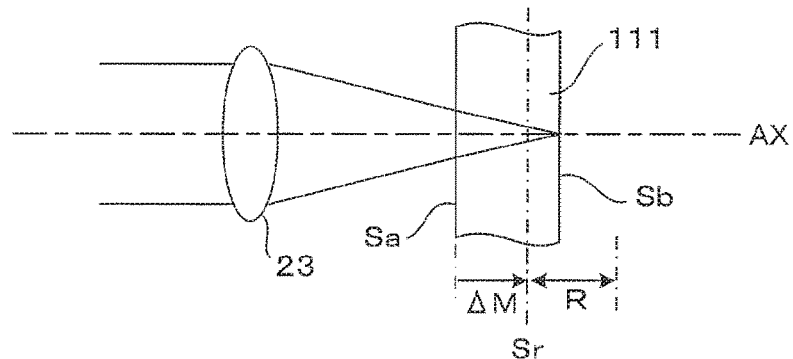
FIG. 12B is a diagram showing how to obtain the optical thickness when the container bottom part is thick.
Figure 12C:
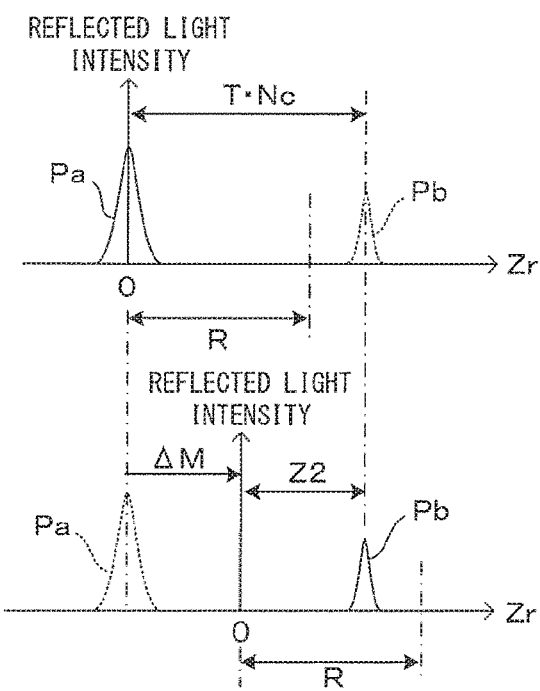
FIG. 12C is a graph showing how to obtain the optical thickness when the container bottom part is thick.

FIGS. 12A, 12B and 12C are diagrams and a graph showing how to obtain the optical thickness when the container bottom part is thick. As shown in FIG. 12A, reference light from a reflecting surface in a predetermined imaging range R from the reference plane Sr is detected in OCT imaging. Note that the influence of complex conjugate signals is not considered here. If the thickness T of the container bottom part 111 is larger than a dimension of the imaging range R, reflected light from the upper bottom surface Sb cannot be detected with the reference plane Sr matched with the lower bottom surface Sa. In this case, the upper bottom surface Sb is included in the imaging range R by shifting the reference mirror 24 by a distance ΔM to change the reference optical path length as shown in FIG. 12B. By doing so, the reference light from the upper bottom surface Sb can be detected.

As shown in FIG. 12C, since an origin is shifted by a shift amount of the reference optical path length in a profile of the reflected light intensity distribution, an optical path length difference between the lower bottom surface Sa and the upper bottom surface Sb, i.e. the optical thickness T·Nc of the container bottom part 111, can be calculated by adding a shift amount ΔM to a distance Z2 between the position of the signal component Pb corresponding to the upper bottom surface Sb and the origin in the shifted profile. On the other hand, the condition for focusing the objective optical system 23 on the upper bottom surface Sb is not affected by the reference optical path length. Thus, the focus position adjustment amount at which the signal component Pb reaches a local maximum can be set as the second adjustment amount OP2 regardless of the shift amount.

Referring back to FIG. 11, the flow chart is further described. By the process thus far, the parameters OP2, Lo and T·Nc included in the equation (5) are respectively obtained. The other parameters Lr, Zf and OP3 are determined during imaging, and the refractive index Ns has a value unique to the culture medium M used. Thus, all the parameters that should be obtained before imaging are already obtained.

Note that, although it is not essential in imaging, the values OP1, OP2 and T·Nc are already specified and, hence, the thickness T and the refractive index Nc of the container 11 can be respectively calculated using these values and the equation (1) (Step S112).

Figure 13:
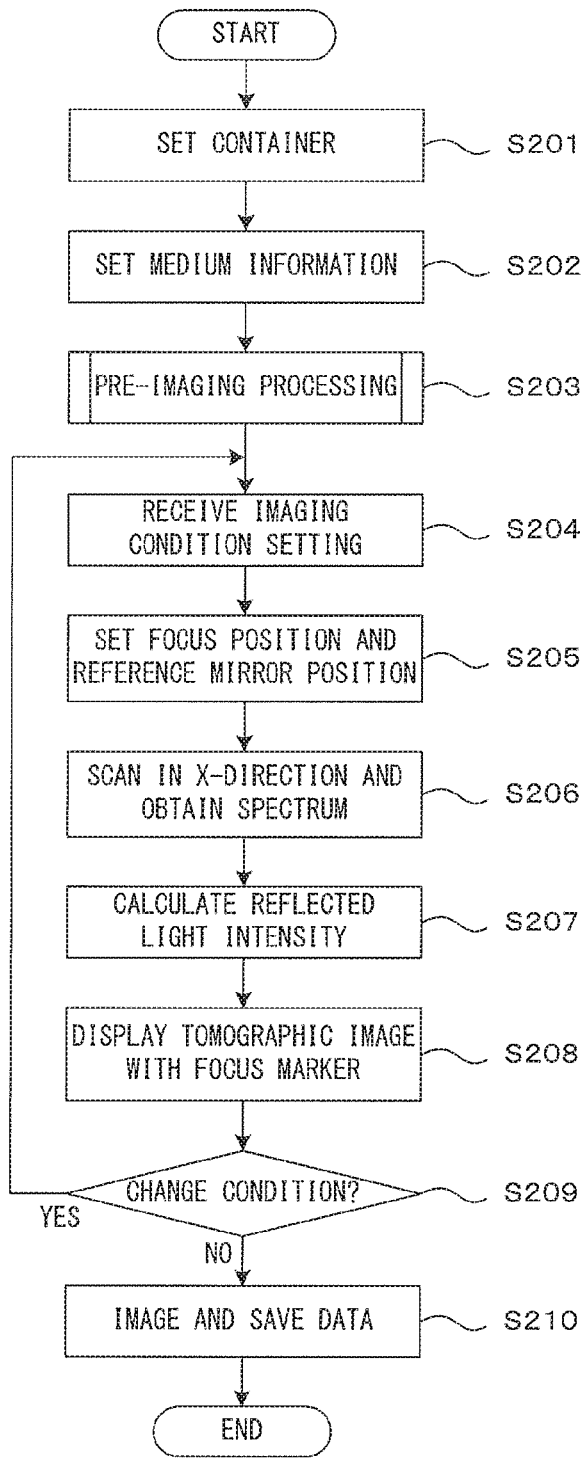
FIG. 13 is a flow chart showing an imaging process in this imaging apparatus.

FIG. 13 is a flow chart showing an imaging process in this imaging apparatus. If the container 11 containing the imaging object in the culture medium M is set in the holder 10 (Step S201), the CPU 31 executes the control program stored in advance and causes each part of the apparatus to perform the following operations, whereby the imaging process is realized. First, input of culture medium information about the culture medium M in the container 11 by the user is received (Step S202). The culture medium information is information necessary to specify the refractive index of the culture medium M used and may be a numerical value of the refractive index or information specifying the type of the culture medium. If a table associating the types and refractive indices of culture media is prepared, the refractive index can be specified from the input type of the culture medium by referring to this table.

Further, refractive indices of culture mediums generally used are substantially about 1.33 to 1.37 for the purpose of culturing cells and tissues and do not largely differ depending on the types of the culture media. Thus, a specified value determined in advance may be used for the refractive index of the culture medium M.

Subsequently, a pre-imaging processing is performed to specify a relationship between a focus position and a reference optical path length (Step S203). A flow of specific processings (FIG. 11) of the pre-imaging processing is as previously described. By the pre-imaging processing, the respective parameters, i.e. the first adjustment amount OP1, the second adjustment amount OP2 and the optical thickness T·Nc of the container 11, are specified according to the container 11 used.

When the pre-imaging processing is finished, the imaging object in the container 11 can be imaged. First, inputs about conditions during imaging set by the user are received (Step S204). Main imaging conditions to be set are the focus position adjustment amount, i.e. the third adjustment amount OP3, of the objective optical system 23 and the position of the reference mirror 24, i.e. the reference optical path length Lr. However, these conditions may be temporarily set values at this point of time and, particularly, an initial value determined in advance may be used for the reference optical path length Lr. For example, the focal depth Zf in an image may be set as half the height of the image. In this way, a range having substantially equal breadths in the vertical direction from the focus position as a center is displayed in the tomographic image. Thus, a fine adjustment of the focus position is easily made by the user. According to these settings, the focusing mechanism 41 drives the objective optical system 23 to set the focus position and the mirror driving mechanism 42 sets the position of the reference mirror 24 (Step S205).

Then, the imaging unit 20 obtains spectrum information of the interference light while optically scanning in the X direction (Step S206) and the signal processor 33 calculates a reflected light intensity distribution based on the obtained spectrum information (Step S207), whereby a tomographic image along one XZ cross-section scanned with light out of the imaging object is generated. The generated tomographic image is presented to the user by being displayed on a display unit 352 together with a marker indicating the focus position (Step S208).

The user can adjust the imaging range and the focus position by viewing the displayed image. Specifically, an image of a part of the imaging object included in the imaging range appears in the tomographic image and the focus position is clearly specified by the marker. If the user wants to change the focus position and the imaging range by viewing this, an input to that effect can be set via the input device 351. Further, if a display mode of fixing the focus position in the image is selected by the user, the position of the reference mirror 24 is automatically adjusted according to the setting of the focus position in accordance with the equation (5). If the user wishes to change these imaging conditions, return is made to Step S104 (YES in Step S209) and the imaging conditions are set again.

Such adjustments of the imaging conditions are repeated, and final imaging is performed under the set imaging conditions (Step S210) if no more change is necessary (NO in Step S209). Imaging at this time may be imaging for one XZ cross-section or may be imaging for a plurality of XZ cross-sections at incident positions of the illumination light different in the Y direction. Data of the tomographic image(s) obtained by imaging is stored in the image memory 36. In the case of performing imaging for a plurality of XZ cross-sections, the 3D restoration section 34 generates a three-dimensional image of the imaging object from those pieces of tomographic image data if necessary.

As described above, this embodiment relates to the imaging apparatus 1 for OCT-imaging the imaging object in the culture medium M carried in the container 11 having the wall part (bottom part 111) optically transparent to illumination light. In this imaging apparatus 1, various pieces of information on the container 11 are obtained by the pre-imaging processing, whereby the influence of refraction by the container 11 can be eliminated and the in-focus position of the objective optical system 23 in the tomographic image can be specified.

Thus, the user can know at which position focusing is achieved for the imaged tomographic image and can evaluate the image precisely. Further, by indicating the in-focus position by the marker in the tomographic image displayed in real time, it is possible to easily adjust the focus position with respect to the imaging object and set the focus position in the tomographic image. Further, if the focus position to be displayed in the tomographic image is set in advance, the reference optical path length can be automatically set according to the adjustment of the focus position with respect to the imaging object by the user. As just described, the imaging apparatus 1 of this embodiment can provide a suitable tomographic image corresponding to the user's wish even if the user does not have detailed knowledge on the imaging principle.

As described above, in the imaging apparatus 1 of the above embodiment, the imaging unit 20 functions as a "imaging unit" of the invention, and the focusing mechanism 41 and the mirror driving mechanism 42 respectively function as a "focus position adjuster" and a "mirror position adjuster" of the invention. Further, the signal processor 33 functions as a "signal processor" of the invention and the CPU 31 functions as a "focus position calculator" of the invention. Further, the display unit 352 functions as a "display unit" and a "display device" of the invention, whereas the input device 351 functions as a "receiver" of the invention. Further, the shutter 27 corresponds to a "shutter member" of the invention.

Further, in the above embodiment, the lower bottom surface Sa of the container 11 corresponds to a "first principal surface" and a "first reflecting surface" of the invention, whereas the upper bottom surface Sb corresponds to a "second principal surface" and a "second reflecting surface" of the invention. Further, the optical thickness T·Nc of the container 11 obtained by measurement corresponds to a "first distance" and the value Zrf expressed by the equation (3) or (4) corresponds to a "second distance" of the invention. Further, the culture medium M of the above embodiment corresponds to a "medium" of the invention.

Note that the invention is not limited to the above embodiment and various changes other than those described above can be made without departing from the gist of the invention. For example, in the description of the above embodiment, the focus position is derived with the lower bottom surface Sa of the container 11 set as a positional reference and the equations (3) and (4) are obtained. This is because the position of the lower bottom surface Sa of the container 11 is thought to be appropriate as a direct positional reference since the position of the lower bottom surface Sa can be specified without being affected by the thickness and the refractive index of the container bottom part 111. However, since the position of the upper bottom surface Sb of the container 11 can be indirectly specified by the pre-imaging processing as described above, the focus position may be specified with the upper bottom surface Sb set as a positional reference. In this case, the focus position can be expressed by the first term on the right side of the equation (4). Which position is used as a reference to express the focus position is arbitrary and a process substantially equivalent to the above technical concept can be realized by appropriately modifying each equation according to the reference position.

Further, in the above embodiment, the imaging unit 20 images the imaging object from below via the bottom part 111 of the container 11 carrying the imaging object. However, an imaging direction is not limited to the above direction and is arbitrary. The above technique is applicable even if imaging is, for example, performed via a side wall of the container.

Further, the imaging apparatus 1 of the above embodiment is an imaging apparatus based on the FD-OCT imaging principle. However, without being limited to FD-OCT, the technical concept of the invention can be applied to various tomographic imaging techniques utilizing interference of light.

Further, in the above embodiment, the position where the signal component is locally maximized in the reflected light intensity distribution obtained from the interference signal output from the photo-detector 26 is searched to specify the in-focus position of the objective optical system 23 on the upper bottom surface Sb of the container 11. Instead of this, the reference light may be shielded by the shutter 27 and the reflected light from the upper bottom surface Sb may be directly detected as in the case of searching an in-focus position on the lower bottom surface Sa. However, detection is thought to become difficult due to the superimposition of the reflected light from the lower bottom surface Sa. Thus, the above embodiment is more preferable in terms of stable detection.

Further, for example, the imaging object of the above embodiment is the spheroid Sp carried in the container 11 called a dish in the form of a shallow plate. However, the types of the imaging object and the container for carrying the imaging object are not limited to these. For example, cells or the like cultured in a well plate in which a plurality of wells capable of carrying specimens are provided on one plate may be imaging objects.

Further, the above embodiment is described on the assumption that the entire spheroid Sp serving as the imaging object is accommodated in the imaging range in the depth direction of the imaging unit 20. On the other hand, there is also a method for obtaining a tomographic image in a wide range by synthesizing partial images imaged with an imaging range changed in a depth direction. Particularly, if the objective optical system 23 is required to have a high magnification or a high resolution, the depth of field of the objective optical system becomes shallower. Thus, even with an FD-OCT device originally capable of wide imaging in a depth direction, a range of an image in the depth direction obtained by one imaging is limited. Even in such a case, a tomographic image covering a wide range and having good image quality can be obtained by synthesizing the partial images respectively imaged by the above technique.

Further, a general-purpose processing apparatus having a general configuration such as a personal computer or work station can be used as the control unit 30 of the above embodiment. Specifically, the image processing apparatus 1 may be configured by combining the imaging apparatus including the imaging unit 20 and the drive controller 40 and having a minimum control function for operating these and a personal computer or the like functioning as the control unit 30 by executing a control program describing the above processing contents.

As the specific embodiment has been illustrated and described above, the first reflecting surface on which the intensity of the signal light is maximized may be searched by detecting the signal light while changing the focus position adjustment amount of the objective optical system in the optical axis direction, and the first reflecting surface may be regarded as the first principal surface in the imaging method according to this invention. According to such a configuration, a first principle surface can be easily specified without being affected by a refractive index also for unknown containers.

Further, for example, the reference mirror may be positioned at such a position that the object optical path length and the reference optical path length to the first principal surface are equal when the focus position adjustment amount of the objective optical system is the first adjustment amount, the second reflecting surface on which the intensity of the reflected light is locally maximized on a side closer to the imaging object than the first reflecting surface may be searched by detecting the interference light while changing the focus position adjustment amount of the objective optical system, and the second reflecting surface may be regarded as the second principal surface. According to such a configuration, the reflected light from the second principal surface can be detected separately from the reflected light from the first principal surface and conditions for focusing on the second principal surface can be more accurately found.

In this case, if the reflected light from the second reflecting surface is not detected, a search may be conducted, for example, by changing the position of the reference mirror in a direction to make the reference optical path length longer. According to such a configuration, the second reflecting surface can be reliably found by changing the reference optical path length even if the wall part thickness of the container is larger than the optical path length difference at which the signal light and the reference light can interfere with each other.

Further, for example, the imaging apparatus according to the invention may be configured such that an openable and closable shutter member is provided on the optical path of the reference light. According to such a configuration, the interference light of the reference light and the signal light can be generated in an open state of the shutter member to allow the passage of the reference light. Further, in a closed state of the shutter member to shield the reference light, only the signal light can be detected and conditions for focusing the objective optical system on the first principal surface can be easily found out.

Further, for example, the imaging method according to the invention may be configured to display a tomographic image added with information representing the focus position on the display device. Further, the imaging apparatus according to the invention may include a display unit for displaying a tomographic image, for example, added with information representing a focus position. According to such a configuration, an in-focus position during imaging can be presented to the user.

Further, for example, a set input about the third adjustment amount may be received and the focus position adjustment amount of the objective optical system may be set according to the set input. According to such a configuration, the user can perform imaging with the focus position during imaging set at a desired position.

Further, for example, the third adjustment amount may be set according to the received set input and the position of the reference mirror may be changed corresponding to the set value of the third adjustment amount. According to such a configuration, since the reference optical path length is automatically set by the user adjusting the focus position, the adjustment operation by the user can be effectively assisted.

INDUSTRIAL APPLICABILITY

This invention can be applied to OCT imaging techniques in general. Particularly, this invention can be suitably applied in the fields of medicine, biochemistry and drug discovery to image cells and cell clusters cultured in a container such as a dish.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

REFERENCE SIGNS LIST

1 image processing apparatus (imaging apparatus)
11 container
20 imaging unit)
27 shutter (shutter member)
31 CPU (focus position calculator)
33 signal processor (signal processor)
40 drive controller
41 focusing mechanism (focus position adjuster)
42 mirror driving mechanism (mirror position adjuster)
111 bottom part (of the container 11) (wall part)
Sa lower surface (of the container 11) (first principle surface, first reflective surface)
Sb upper surface (of the container 11) (second principle surface, second reflective surface)
Sf focal plane
Sp spheroid (imaging object)
Sr reference plane

The invention claimed is:

1. An imaging method for tomographically imaging an imaging object in a medium carried in a container having an optically transparent wall part, the imaging method comprising:
 causing one branch light branched from low coherence light emitted from a light source to be incident on the imaging object, causing interference of signal light obtained by condensing reflected light from the imaging object via the wall part by an objective optical system and reference light obtained by reflecting another branch light by a reference mirror and obtaining an interference signal corresponding to a detection result of interference light;

obtaining a reflected light intensity distribution of the imaging object based on the interference signal and generating a tomographic image from the reflected light intensity distribution; and specifying a focus position of the objective optical system in the tomographic image, wherein when:

an object optical path length is defined as an optical path length of the signal light;

a reference optical path length is defined as an optical path length of the reference light;

a first adjustment amount is defined as a focus position adjustment amount of the objective optical system when the objective optical system is focused on a first principal surface on a side of the objective optical system out of principal surfaces of the wall part;

a second adjustment amount is defined as a focus position adjustment amount of the objective optical system at which an intensity of reflected light from a second principal surface on a side of the imaging object out of the principal surfaces of the wall part is maximized when the reference mirror is positioned at a position where the reference optical path length is equal to the object optical path length to the first principal surface with the focus position adjustment amount of the objective optical system set at the first adjustment amount; and a first distance is defined as a distance between the first principal surface and the second principal surface in an optical axis direction of the objective optical system in the reflected light intensity distribution obtained from the interference signal, a position where a distance to the first principal surface in the optical axis direction in the reflected light intensity distribution obtained from the interference signal obtained with the focus position adjustment amount of the objective optical system set at a third adjustment amount, the second adjustment amount being between the first adjustment amount and the third adjustment amount, is a second distance expressed by a sum of a value obtained by multiplying a difference between the third adjustment amount and the second adjustment amount by a square of a refractive index of the medium and the first distance is set as a focus position of the objective optical system in the tomographic image corresponding to the reflected light intensity distribution.

2. The imaging method according to claim 1, wherein a first reflecting surface on which the intensity of the signal light is maximized is searched by detecting the signal light while changing the focus position adjustment amount of the objective optical system in the optical axis direction, and the first reflecting surface is regarded as the first principal surface.

3. The imaging method according to claim 1, wherein the reference mirror is positioned at such a position that the reference optical path length is equal to the object optical path length to the first principal surface when the focus position adjustment amount of the objective optical system is set at the first adjustment amount, the second reflecting surface on which the intensity of the reflected light is locally maximized on a side closer to the imaging object than the first reflecting surface is searched by detecting the interference light while changing the focus position adjustment amount of the objective optical system, and the second reflecting surface is regarded as the second principal surface.

4. The imaging method according to claim 3, wherein if the reflected light from the second reflecting surface is not detected, a search is conducted by changing the position of the reference mirror in a direction to make the reference optical path length longer.

5. The imaging method according to claim 1, wherein the tomographic image added with information representing the focus position is displayed on a display device.

6. The imaging method according to claim 1, wherein the third adjustment amount is set according to a set input received from a user and the position of the reference mirror is set corresponding to the third adjustment amount.

7. An imaging apparatus for tomographically imaging an imaging object in a medium carried in a container having an optically transparent wall part, the imaging apparatus comprising:

an imaging unit which causes one branch light branched from low coherence light emitted from a light source to be incident on the imaging object, detects interference light generated by interference of signal light obtained by condensing reflected light from the imaging object via the wall part by an objective optical system and reference light obtained by reflecting another branch light by a reference mirror and outputs an interference signal corresponding to the detected interference light;

a signal processor which obtains a reflected light intensity distribution of the imaging object based on the interference signal and generates a tomographic image from the reflected light intensity distribution;

a focus position adjuster which changes a focus position of the objective optical system in an optical axis direction of the objective optical system;

a mirror position adjuster which changes a position of the reference mirror in a direction along an optical path of the reference light;

and a focus position calculator which calculates a focus position of the objective optical system in the tomographic image, wherein when:

an object optical path length is defined as an optical path length of the signal light;

a reference optical path length is defined as an optical path length of the reference light;

a first adjustment amount is defined as a focus position adjustment amount of the objective optical system by the focus position adjuster when the objective optical system is focused on a first principal surface on a side of the objective optical system out of principal surfaces of the wall part;

a second adjustment amount is defined as a focus position adjustment amount of the objective optical system by the focus position adjuster at which an intensity of reflected light from a second principal surface on a side of the imaging object out of the principal surfaces of the wall part is maximized when the reference mirror is positioned by the mirror position adjuster at a position where the reference optical path length is equal to the object optical path length to the first principal surface with the focus position adjustment amount of the objective optical system set at the first adjustment amount; and a first distance is defined as a distance between the first principal surface and the second principal surface in an optical axis direction of the objective optical system in the reflected light intensity distribution obtained from the interference signal by the focus position calculator, the focus position calculator sets, as the focus position of the objective optical system in the tomographic image corresponding to the reflected light intensity distribution, a position where a distance to the first principal surface in the optical axis direction in the reflected light intensity distribution obtained from the interference signal obtained with the focus position adjustment amount of the objective optical system set at a third adjustment amount, the second adjustment amount being between the first adjustment amount and the third adjustment amount, is a second distance expressed by a sum of a value obtained by multiplying a difference between the third adjustment amount and the second adjustment amount by a square of a refractive index of the medium and the first distance.

8. The imaging apparatus according to claim 7, further comprising a shutter member which is openable and closable and provided on the optical path of the reference light.

9. The imaging apparatus according to claim 7, further comprising a display unit which displays the tomographic image added with information representing the focus position.

10. The imaging apparatus according to claim 1, further comprising a receiver which receives a set input about the third adjustment amount from the user, wherein the focus position adjuster set the focus position adjustment amount of the objective optical system according to the set input.

11. The imaging apparatus according to claim 10, wherein the receiver receives a set input for changing the position of the reference mirror, and the mirror position adjuster sets the position of the reference mirror according to the set input.

12. The imaging method according to claim 2, wherein
the reference mirror is positioned at such a position that the reference optical path length is equal to the object optical path length to the first principal surface when the focus position adjustment amount of the objective optical system is set at the first adjustment amount,
the second reflecting surface on which the intensity of the reflected light is locally maximized on a side closer to the imaging object than the first reflecting surface is searched by detecting the interference light while changing the focus position adjustment amount of the objective optical system, and
the second reflecting surface is regarded as the second principal surface.

13. The imaging apparatus according to claim 8, further comprising a display unit which displays the tomographic image added with information representing the focus position.

* * * * *